United States Patent [19]
Raleigh et al.

[11] Patent Number: 5,405,760
[45] Date of Patent: Apr. 11, 1995

[54] PROCESS FOR PRODUCING RECOMBINANT MCRBC ENDONUCLEASE AND CLEAVAGE OF METHYLATED DNA

[75] Inventors: Elisabeth A. Raleigh, West Somerville; Ellen S. Hauck, Lowell, both of Mass.

[73] Assignee: New England Biolabs, Inc., Beverly, Mass.

[21] Appl. No.: 876,793

[22] Filed: Apr. 30, 1992

[51] Int. Cl.$^6$ .................... C12N 9/22; C12N 15/55; C12N 15/70
[52] U.S. Cl. ..................... 435/91.53; 435/199; 435/252.33; 435/320.1; 536/23.2
[58] Field of Search ............. 435/91, 199, 320.1, 435/252.33; 536/23.2

[56] References Cited
U.S. PATENT DOCUMENTS
5,082,784  1/1992  Chatterjee et al. ............. 435/252.3

OTHER PUBLICATIONS
Sutherland, E. et al., (1992), J. Mol. Biol., 225, 327–348.
Zheng, L., et al., (1992), Gene, p. 112, 97–100.

*Primary Examiner*—Charles L. Patterson, Jr.
*Attorney, Agent, or Firm*—David G. Conlin; Gregory D. Williams; Peter F. Corless

[57] ABSTRACT

The present invention relates to a recombinant McrBC endonuclease obtainable from Escherichia coli, two components of which, McrB$_L$ and McrC, have been purified in active form. McrBC is active in the presence of GTP and at a low pH. The McrBC endonuclease is also substantially free of a third component, McrB$_S$, which is believed to inhibit or otherwise interfere with the activity of the enzyme. McrBC has various desirable properties, including the ability to recognize a methylated DNA sequence and also its ability to cleave such a sequence in the presence of GTP. Also provided is a process for the production of recombinant McrBC endonuclease, a process for the determination of the modification state of DNA a process for the determination of an epigenetic alteration or defect (including "imprinting"), as well as a process for identifying and isolating additional enzymes that cleave modified DNA.

17 Claims, 11 Drawing Sheets

Potential translation start sites:

McrB_L

-15
```
              *                     *
              M  R  K  A  Y  L  M  E  S
AATAGAGGCTTAGCAATGAGGAAGGCATATCTTATGGAATCT...
```

McrC

1355
```
                                        *
  M  D  Q  Q  I  R  G  L  I  V  E  Q  P  V  I
* 
TAAACAACAGAAATGGACCAACAAATTATTAGGGACTCATAGTGGAACAGCCCGTGATA...
```

FIG. 10

PROCESS FOR PRODUCING RECOMBINANT MCRBC ENDONUCLEASE AND CLEAVAGE OF METHYLATED DNA

BACKGROUND OF THE INVENTION

The present invention relates to a DNA endonuclease, McrBC, obtainable from Escherichia coli, two components of which have been purified in active form. The present invention also relates to the process for detecting and cleaving methylated DNA with said endonuclease. Other related processes are disclosed, including a process for the determination of the modification state of DNA, a process for the determination of epigenetic alterations as well as a process for identifying and isolating additional enzymes that cleave modified DNA.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Typically, cells expressing a restriction endonuclease also elaborate a cognate modification methylase, which recognizes the same sequence as does the endonuclease and methylates a specific base within that sequence. This modification renders the DNA resistant to cleavage by the cognate endonuclease (Bickle, I.A. Amer. Society for Molecular Biology, 692–696 (1987); Modrich & Roberts, Nucleases, 109–154 (1982)). Consequently, the DNA of most bacteria is modified at specific sequences, but the sequences modified are different for different strains and species because they carry different restriction enzymes. DNA of many eukaryotic organisms, including all mammals and higher plants, is also modified to contain 5-methylcytosine (m5C) in 5'CG3' or 5'CNG3' sequence contexts. In these cases, no restriction enzymes are found, and the role of modification is thought to be regulation of gene expression (Ehrlich & Wang, Science, 212:163–170 (1981)).

One example is known of a restriction endonuclease that recognizes a modified sequence, rather than an unmodified one; this enzyme (DpnI and isoschizomers) cleaves only DNA containing the sequence GmATC, where mA is $N^6$-methyladenine (Lacks & Greenberg, J. Biol. Chem. 250:4060–4066 (1975); Lacks & Greenberg, J. Mol. Biol., 114:153–168 (1977)). This enzyme has been used extensively to detect GmATG modification in DNA from enteric bacteria wherein methylation of this sequence regulates DNA repair and replication (Barbeyron et al., J. Bacteriol., 160:586–590 (1984); Russell & Zinder, Cell, 50:1071–1079 (1987); Messer & Noyer-Weidner, Cell, 54:735–737 (1988)). as well as from other sources. No other methylation pattern can be analyzed in this way since no other modification-specific restriction enzyme has been described.

Also, many other nucleases exist besides the restriction endonucleases Linn & Roberts, Nucleases, Cold Spring Harbor Laboratory Press (1982)), which possess widely varying properties. However, only a small number of different co-factor requirements have been described. Nucleases often, but not always require a divalent cation, which may be $Mg^{++}$ or $Ca^{++}$, or in some cases $Mn^{++}$. Nucleases frequently require ATP, which in a few cases can be replaced by a non-hydrolyzable analogue of ATP, for example ATP-gamma-S or AMP-PNP or AMP-PCP. One example has been described in which GTP will satisfy the nucleotide requirement of an ATP-dependent nuclease, but the nuclease acts much less efficiently with GTP than with ATP (Goldmark & Linn, J. Biol. Chem., 247:1849–1860 (1972)). No nuclease which requires GTP rather than ATP has been, to date, isolated in an active, commercially useful form. In addition, as discussed below, in accordance with the present invention, McrBC is the only nuclease that will not use ATP since ATP acts as an inhibitor of its activity.

The McrBC restriction system, formerly known as RglB, (Raleigh et al., J. Cell. Biochem., suppl. 16B, 21 (1992)), was first discovered in 1952 (Luria & Human, J. Bacteriol., 64:557–559 (1952)) and was investigated by genetic methods in the 1960's (Georgopoulos & Revel, Virology, 44:271–285 (1971); Georgopoulos, Biochem. Biophys. Res. Commun., 28:179–184 (1967); Revel, Virology, 31:688–701 (1967); Revel et al., Biochem. Biophys. Res. Commun., 18:545–550 (1965); Revel & Hattman, Virology, 45:484–495 (1971)). It was found that the restriction of T-even phage seen in vivo depended both upon incorporation into DNA of the unusual base 5-hydroxymethylcytosine (hmC) and upon failure to further modify the hmC by glucosylation due to phage or host mutations. This system was designated Rgl reflecting the fact that it restricts glucoseless phage.

In the mid-80's, several groups reported restriction of DNA methylated by sequence-specific cytosine methylases (Noyer-Weidner et al., Mol. Gen. Genet., 205:469–475 (1986); Raleigh & Wilson, Proc. Natl. Acad. Sci. USA, 83:9070–9074 (1986)). This was designated Mcr restriction, for modified cytosine restriction. The mcrB-dependent restriction was shown to be genetically identical with the above-described rglB-dependent restriction (Raleigh et al., Genetics 122:279–296 (1989)). Demonstration of this restriction effect explained previous observations that the genes for many DNA modification methylases could not be cloned in some strains (Blumenthal et al., J. Bacteriol., 164:501–509 (1985); Kiss & Baldauf, Gene, 21:111–119 (1983)), and that DNA from diverse organisms could be cloned only with low efficiency and in biased fashion (Whittaker et al., Nucleic Acids Res., 16:6725–6736 (1988); Woodcock et al., Nucleic Acids Res., 17:3469–3478 (1989)).

The genes involved (mcrBC) were cloned (Krüger et al., Gene, (1991); Raleigh et al., Genetics, 122:279–296 (1989); Ross et al., Gene, 61:277–289 (1987); Sozhamannan & Dharmalingam, Curr. Microbiol., 17:269–273 (1988); Sozhamannan & Dharmalingam, Gene, 74:51–52 (1988)) and sequenced (Dila et al., J. Bacteriol., 172:4888–4900 (1990); Ross et al., J. Bacteriol., 171:1974–1981 (1989b)). It was shown that two genes were required for restriction (Dila & Raleigh, Gene, 74:23–24 (1988); Dila et al., J. Bacteriol., 172:4888–4900 (1990); Ross et al., Mol. Gen. Genet., 216:402–407 (1989a)) and that the two genes directed expression of three proteins (Dila et al., J. Bacteriol., 172:4888–4900 (1990); Krüger et al., Gene, in press (1991); Ross et al., Mol. Gen. Genet., 216:402–407 (1989a)). A possible GTP-binding motif was identified in the amino acid sequence of McrB (Dila et al., J. Bacteriol., 172:4888–4900 (1990)). However, there existed uncertainty concerning the precise position of translation initiation. (Dila et al., J. Bacteriol., 172:4888–4900 (1990); Krüger et al., Gene, in press (1991); Ross et al., Gene, 61:277–289 (1987); Ross et al., Mol. Gen. Genet., 216:402–407 (1989a)). Two start sites have been proposed for McrB$_L$ (one of two protein products produced by the mcrB gene) and McrC: Ross et al. (Ross et al., J. bacteriol. 171:1974–1981 (1989b)) chose starts based on potential Shine/Dalgarno sequences, while Dila et al (Dila, et al., J. Bacteriol. 172:4888–4900 (1990)) arbitrarily chose the first methionine of the frame. The potential translation starts are shown in FIG. 10 (SEQ ID No:1 and SEQ ID NO:2). As disclosed in more detail below, the construct of the present invention used to overproduce the McrB component elaborates only one of two products of the mcrB gene, namely McrB$_L$. As noted above, the mcrB gene encoding McrB$_L$ expresses two protein products, McrB$_L$ and McrB$_S$ in most expression constructs. Translation of McrB$_L$ begins early in the open reading frame (Dila, et al., J. Bacteriol. 172:4888–4900 (1990); Ross, et al., Gene, 61:277–289 (1989)), while translation of McrB$_S$ is in the same reading frame but begins at an internal initiation site (Krüger, et al. Gene, in press (1991); Ross, et al., Gene, 61:277–289 (1987)). The precise N-terminus of McrB$_S$ is not known but a candidate initiation site has been proposed (Ross, et al., Gene, 61:277–289 (1987)).

McrBC-like enzymes are likely to be found in other organisms and may show a degree of conservation. Both E.coli K12 and E.coli B display biological properties expected of strains with an McrBC activity, but these properties show somewhat different specificities for different phages (Raleigh et al., Genetics, 122:279–296 (1989); Revel, Virology, 31:688–701 (1967)). This suggests that the two strains express related enzymes, which may recognize different sequences. The genes for these enzymes cross-hybridize (Daniel et al., J. Bacteriol., 170:1775–1782 (1988)). This situation resembles the case of the EcoK and EcoB enzymes; not only do these closely related genes cross-hybridize, but the enzymes can exchange subunits with retention of function and the polypeptides cross-react antigenically, even though they recognize different specific sequences (Bickle, T. A. Amer. Society for Molecular Biology, 692–696 (1987)).

It is also likely that some members of the McrBC family have diverged in DNA sequence to such a degree that cross-hybridization does not occur. This kind of divergence has occurred with other families of restriction enzymes. For example, restriction enzymes EcoK and EcoA have the same subunit structure, nucleotide dependence and cleavage properties (but different sequence recognition properties) and the chromosomal location of the hsd$_K$ and hsd$_A$ genes is the same, but the genes do not cross-hybridize and the subunits are not exchangeable (Bickle, T. B. Amer. Society for Molecular Biology, 692–696 (1987)).

Little is known of the molecular nature of mcrBC-dependent restriction. Physiological and genetic experiments investigated the fate of RglB-restricted hmC-T4 DNA inside of cells and suggested that this DNA was cleaved by RglB a small number of times (Dharmalingam & Goldberg, Nature, 260:406–410 (1976a)). The small number of cleavages suggested that cleavage might be sequence-specific, but this interpretation was contested, based on physiological considerations (Krüger & Bickle, Microbiol. Rev, 47:345–360 (1983)). The issue was complicated by the demonstration that T4 can express a protein capable of inhibiting the action of RglB in vivo (Dharmalingam & Goldberg, Nature, 260:454–455 (1976b)).

Attempts to characterize the in vitro activity of the enzyme were made in the early 1970's (Eigner & Block, J. Virology, 2:320–326 (1968); Fleishman et al., J. Biol. Chem., 1561–1570 (1976); Fleishman et al., Proc. Natl. Acad. Sci. USA, 68:2527–2531 (1971)). The latter authors demonstrated rglB$^+$-dependent solubilization of circular hmC-containing DNA in crude extracts containing Exonuclease V and concluded from this and other evidence that double-strand breaks were occurring. Purification efforts led to 240-fold purification of a required component but an essential heat-labile, non-dialysable component of the reaction had been lost (Fleishman, et al., J. Biol. Chem., 1561–1570 (1976)). No reports of in vitro activities of the McrBC proteins have appeared since the initial report by Fleishman et al., J. Biol. Chem., 1561–1570 (1976)).

The ability to cleave methylated DNA specifically has been of considerable interest because methylated DNA is widely distributed in nature (Barbeyron et al., J. Bacteriol., 160–586–590 (1984); Ehrlich & Wang, Science, 212:163–170 (1981); Ehrlick et al., J. Bacteriol., 169:939–943 (1987)). It is found in bacteriophage (Trautner et al., Mol. Gen. Genet., 180:361–367 (1980); Warren, Ann. Rev. Microbiol., 34:137–158 (1980)) viruses (van Etten et al., Nucleic Acids Res., 13:3471–3478 (1986)), eubacteria (McClelland & Nelson, Gene, 74:291–304 (1988)), archebacteria (Lunnen et al., Gene, 77:11–19 (1989)), fungi (Mooibroek et al., Mol. Gen. Genet., 222:41–48 (1991); Selker et al., Science, 238:48–53 (1987)), protozoa Capowski et al., Gene, 74:103–104 (1988)), parasites (Pollack et al., Exp. Parasitol., 72:339–344 (1991)) higher plants, Chandler & Walbot, Proc. Natl. Acad. Sci. USA, 83:1767–1771 (1986)), animals Bestor et al., J. Mol. Biol., 203:971–983 (1988)) and cellular organelles (Burton et al., Proc. Natl. Acad. Sci. USA, 76:1390–1394 (1979); Ngernprasirtsiri et al., Cell Struct. Funct., 15:285–293 (1990)).

In bacteria, DNA modification plays an important role in DNA repair and in the timing of replication (Marinus, Ann. Rev. Genet., 21:113–131 (1987); Messer & Noyer-Weidner, Cell, 54:735–737 (1988); Russell & Zinder, Cell, 50:1071–1079 (1987)) as well as regulation of genetic exchange via restriction-modification systems (Modrich & Roberts, Nucleases,, 109–154 (1982); Price & Bickle, Microbiol. Sci., 3:296–299 (1986); Raleigh et al., Raleigh et al., Genetics 122:279–296 (1989)). In eukaryotic organisms DNA methylation is thought to regulate gene expression (Cedar, Cell, 53:3–4 (1988) and abnormal methylation patterns in humans are thought to be associated with the origin of cancer (Nelkin et al., Blood, 77:2431–2434 (1991)), aberrations in development (Holliday, R., Science, 238:163–170 (1987); Oberle et al., Science, 252:1097–1102 (1991); Silva & White, Cell, 54:145–152 (1988)), and genetic disease (Holliday, R. Science, 238:163–170 (1987); Oberle et al., Science, 252:1097–1102 (1991); Silva & White, Cell, 54:145–152 (1988)).

Some genetic diseases are thought to result from the establishment ("imprinting") of aberrant methylation patterns during gametogenesis (egg and sperm development). The term genomic imprinting (Chaillet et al., Cell, 66:77–83 (1991); Solter, Annu. Rev. Genet., 22:127–146 (1988); Surani et al., Philos. Trans. Roy. Soc., (Lond) B 326, 313–327 (1990)) refers to the reversible inactivation of a gene, depending on whether the gene is transmitted through the male or the female parent. That is, a gene may be expressed when it has been inherited from the mother but not when it has been inherited from the father. An inactive gene inherited by a daughter from her father will be reactivated when she passes it to her children (since she is the mother). In other cases, imprinting may occur in the mother, not in the father. Only some genes are subject to imprinting.

In consequence of imprinting, two "defective" genes may be inherited, even when one is wild-type (normal) in sequence. This happens if the wild-type copy is imprinted and thus inactivated, while the non-imprinted copy is mutated at the sequence level; a genetic disease may then result. Diagnosis of genetic disease in such cases will not be possible by the usual sequence-based methods, because non-diseased and diseased individuals cannot be distinguished on the basis of sequence. A non-diseased heterozygote with a mutated, imprinted copy and a wild-type, non-imprinted copy will be indistinguishable from a diseased heterozygote with an wild-type, imprinted copy and a mutated, non-imprinted copy. DNA methylation patterns are closely related to imprinted state, and imprinting may in fact be the same as methylation. Resetting of the imprinted state occurs during gametogenesis (Chaillet, et al., Cell 66:77–83 (1991)) and is associated with changes in DNA methylation of the sequence of the gene and near it (Holliday, R., Science, 238:163–170 (1987); Reik et al., Nature, 328:248–251 (1987); Silva & White, Cell, 54:145–152 (1988)).

The ability to detect DNA methylation readily and accurately is thus desired. Methods for detection of methylation are cumbersome or inaccurate or both. One method used for detection of methylation in mammalian DNA relies on methylation-sensitive enzymes. Methylation of mammalian DNA occurs at some but not all CG dinucleotides, and the presence or absence of methylation may vary depending on the tissue and developmental stage (Cedar, Cell 53:3–4 (1988)). When methylation is present in the vicinity of a gene, many or most CG dinucleotides in the region are modified. Such methylation is usually detected by Southern blot analysis of fragments generated by methylation-sensitive restriction enzymes (Bird & Southern, J. Mol. Biol., 118:27–47 (1978)). The enzymes usually used for this are MspI, which cleaves CCGG whether or not the internal cytosine is methylated, and HpaII, which cleaves the same sequence, but only when the internal C residue is not modified. Cleavage by MspI verifies that a site exists, and failure of HpaII to cleave demonstrates that methylation is present at the particular GG dinucleotide in question. Fragments are visualized by probing with cloned or synthetic probes complementary to the sequence surrounding the site.

A considerable drawback to the above-described method is that only about 1/16 of potentially modified sites can be monitored ($\frac{1}{4}$ of residues 5' to CG will be C and $\frac{1}{4}$ of residues 3' to CG will be G). Failure to detect methylation in a sequence of interest may be due to absence of a suitably located MspI/HpaII site, not to the absence of methylation. Some other pairs of isoschizomers exist (Nelson & McClelland, 1991), but are of limited utility. The pairs XmaI/SmaI (CCCGGG) and AccIII/BspMII (TCCGGA) only detect a subset of the methylation sites detected by MspI/HpaII. The pair AsuII/Csp45I (TTCGAA) detects additional sites, but an even smaller fraction (1/256) of possible sites.

Another method to detect DNA methylation relies on a modification of the Maxam-Gilbert sequencing protocol called genomic sequencing (Church & Gilbert, Proc. Natl. Acad. Sci. USA, 81:1991–1995 (1984)). The method relies on the failure of M5C residues to be cleaved by the Maxam-Gilbert C reaction, resulting in a missing band in the sequence ladder where m5C had been present (Saluz and Jost, Gene, 42:151–157 (1986)). This method can be used only on small stretches of DNA and for best results the sequence must be known, at least sufficiently for design of an oligonucleotide primer to prime synthesis of DNA from within a few hundred basepairs of methylated position. The procedure is long and labor-intensive and is sensitive to reagent contamination.

A third approach relies on converting all C residues except those that are methylated (m5G) to U using sodium bisulfite, followed by amplification by PGR, cloning, and sequencing via the dideoxy chain-termination method (Frommer et al., Proc. Natl. Acad. Sci. USA, 89:1827–1831 (1992)). This procedure yields a positive display of m5C residues—only where m5G residues were present will a band appear in the sequencing ladder—but it otherwise this method suffers similar limitations to the genomic sequencing approach: it requires knowledge of the sequence beforehand, can only be used on short stretches, and is laborious.

In short, better methods for detection of modification are desired.

SUMMARY OF THE INVENTION

In accordance with the present invention, there is provided an endonuclease obtainable from Escherichia coli, hereinafter referred to as "McrBC", two components of which, $McrB_L$ and McrC, have been purified in active form. McrBC is active in the presence of GTP and at a low pH. The McrBC endonuclease of the present invention is also substantially free of a third component, $McrB_S$, which is believed to inhibit or otherwise interfere with the activity of the enzyme. The McrBC endonuclease of the present invention has various desirables properties, including the ability to recognize a methylated DNA sequence and also its ability to cleave such a sequence in the presence of GTP.

The present invention also relates to a process for the production of recombinant McrBC endonuclease. This process comprises isolating DNA coding for the two active components of McrBC, inserting the isolated DNA into the same or separate vectors to form a recombinant vector(s), transforming a host cell with the recombinant vector(s), and culturing the transformed host cells under conditions suitable for expression of the active components of the McrBC endonuclease. In one preferred embodiment, constructs pER273 (McrB) and pER276 (McrC) are used in accordance with the above-described method.

The present invention additionally relates to a process for the determination of the modification state of DNA as well as to a process for the determination of an epigenetic alteration or defect (including "imprinting").

The present invention further relates to a process for identifying and isolating additional enzymes that cleave modified DNA, which at a minimum comprises testing cell extracts for GTP-dependent endonucleolytic activity directed to methylated DNA. Other alternative and/or additional methods which may be employed in the isolation and identification of such endonucleases include: 1) producing an antibody to a purified component described herein (McrB and/or McrC) followed by screening cell extracts of natural organisms for the presence of cross-reacting material, followed by testing for the ability of such material cross-reacting with one component to exhibit endonucleolytic activity in a reaction containing material cross-reacting with the other component; 2) conducting reactions to test endonucleolytic activity at low pH, to wit, less than about pH 6.5 and as low as about 5.5; 3) obtaining a factor that stimulates the McrBC cleavage reaction and its use to stimulate reaction of related enzymes; 4) identifying an McrC-related component in an extract by complementing the reaction with $McrB_L$ and identifying an McrB-related component in an extract by complementing the reaction with McrC; 5) identifying an activity by employing strains deficient in other nucleases that interfere with detection of activity and to do so by cloning genes identified by cross-hybridization with the mcrBC genes into such desirable strains of E.coli K-12; and 6) identifying an activity by employing strains deficient in other nucleases that interfere with detection of activity and to do so by cloning genes identified by cross-hybridization with the mcrBC genes into such desirable strains of E.coli K-12 except for cloning genes identified using degenerate oligonucleotides designed on the basis of the GTP-binding site found in McrB.

The procedure of testing cell extracts for GTP-dependent endonucleolytic activity directed to methylated DNA can be replaced with procedure described 2). All the other procedures listed can be performed prior to and/or in addition to the minimum procedure described above.

BRIEF DESCRIPTION OF THE DRAWING

FIG. 10 (SEQ ID NO: 1 and SEQ ID NO:2) is a diagram showing potential translation start sites for $McrB_L$ and McrC.

DETAILED DESCRIPTION OF THE INVENTION

Figure 1:
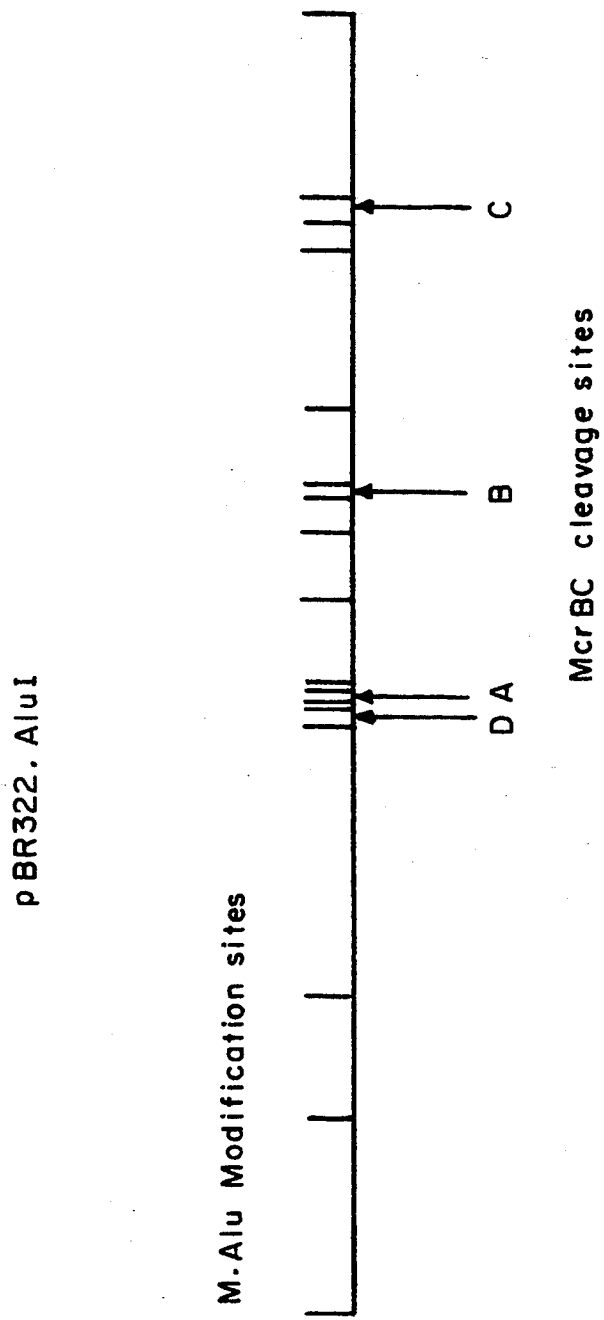
FIG. 1 is a diagram of the substrate pBR322 which is used in FIGS. 2 and 7.

In accordance with one embodiment of the present invention, recombinant McrBC endonuclease, comprising two active components $McrB_L$ and McrC, is provided wherein said recombinant McrBC is substantially free of $McrB_S$. More specifically, nucleic acid sequences encoding $McrB_L$ and McrC are inserted into one or more plasmids to form recombinant vectors, which recombinant vectors are introduced into one or more host cells and cultivated under conditions suitable for expression of said active components. Where the DNA coding for the two active components is introduced into two separate plasmids, it is preferred that separate host cells be employed. The same host cell can be employed if the respective plasmids carrying the DNA encoding the active components have suitable replication origins and selection markers.

In one preferred embodiment, Escherichia coli strains BL21(DE3)/pER273 (expressing McrB) and BL21 (DE3)/pER276 (expressing McrC) are cultured and the components of the endonuclease recovered. A sample of each strain has been deposited with the American Type Culture Collection (ATCC) on Apr. 29, 1992, bearing the Accession Nos. 68969 and 68970, respectively.

For recovering the enzyme of the present invention, E.coli, such as the strains described above, may be grown using any suitable technique. For example, E.-coli may be grown in a medium comprised of 10 g/L tryptone, 5 g/L yeast extract, 10 g/L NACl, 1 g/L dextrose, 1 g/L MgCl2.6H2O (pH 7.2), which is incubated at 37° C. with agitation and aeration. Cells in the late logarithmic stage of growth may be induced if appropriate, for example by addition of isopropyl-$\beta$-D-thiogalactoside, collected by centrifugation and either disrupted immediately or stored frozen at −70° C.

$McrB_L$ and McrC can be isolated from the E.coli strains described above by conventional protein purification techniques. For example, cell paste from the two strains may be suspended in a buffer solution and treated by sonication, high pressure dispersion or enzymatic digestion to allow extraction of the endonuclease components by the buffer solution. Intact cells and cellular debris are then removed by centrifugation to produce cell-free extracts containing McrB and McrC. The two components of the McrBC endonuclease are then purified from the cell-free extracts by ion-exchange chromatography, affinity chromatography, molecular sieve chromotography, or a combination of these methods to produce the endonuclease of the present invention.

Alternatively, a construct expressing both $McrB_L$ and McrC from the same plasmid can be created by digestion of pER276 with SphI and AatII, purifying the smaller fragment, repairing the ends with T4 DNA polymerase, and ligating this into AatII-digested pER273 with the 3' extensions repaired with T4 DNA polymerase. This will yield a plasmid with both mcrB and mcrC genes separately under the control of the T7 gene 10 promoter. Preferably, this proposed construct will be introduced into Rec⁻ strain that is a derivative of BL21(DE3), which derivative can be constructed by P1 transduction using NK8057 (recA::Cam) as donor, selecting for chloramphenicol resistance, repurifying to single colonies and verifying successful construction by testing transductants for increased sensitivity to ultraviolet light.

McrBC may also be expressed from pDD10 which is a low copy plasmid and, a derivative of pBR322. This plasmid carries a BamHI-EcoRi fragment including the mcrB and mcrC genes inserted between the EcoRI and BamHi sites of pBR322. The amount of each component of the enzyme expressed from this plasmid is at least 25,000-fold less than the amount expressed from the constructs pER273 and pER276 but is at least 5 times more than the amount expressed from the native wild-type strain.

The activity of the McrBC enzyme as used herein is the ability of two components, $McrB_L$ and McrC together, to recognize modified cytosine in a specific sequence context, namely $R^mC(N40-100)R^mC$, and to cause breaks in both strands of the DNA in the region between the two modified bases. This activity can be recognized by cleavage of ClaI-digested pBR322.AluI (containing modified cytosine only in AluI sites) at positions between 2043–2092, between 2032–2092, between 2708–2754, between 3688–3695, and between 1975–2032 (see TABLE I below). This activity results in the appearance of partially-cleaved fragments of 2.3, 2.0, 1.6, 0.9, 0.7, 0.6 kb and of completely-digested fragments of 2.0, 0.85, 0.7 and 0.6 kb.

One unit of activity is therefore defined as the amount of enzyme or subunit required fully to cleave the 2.3 kb partial digest product of 0.2 mg pBR322.AluI in 30 minutes at 37° C. in the presence of 1 mM GTP and a standard amount of the other subunit, if appropriate.

The above definition of McrBC activity is complicated by the fact that both an $McrB_L$ component and an McrC component must be added, and the activity observed depends on the concentration of each. The units and specific activity so defined for one component are defined for a specific preparation of the other component. Therefore present, units can be interpreted only relative to other fractions of the same component measured in the presence of the same preparation of the other component. A unit of McrB has no necessary relationship to a unit of McrC.

Figure 2A:
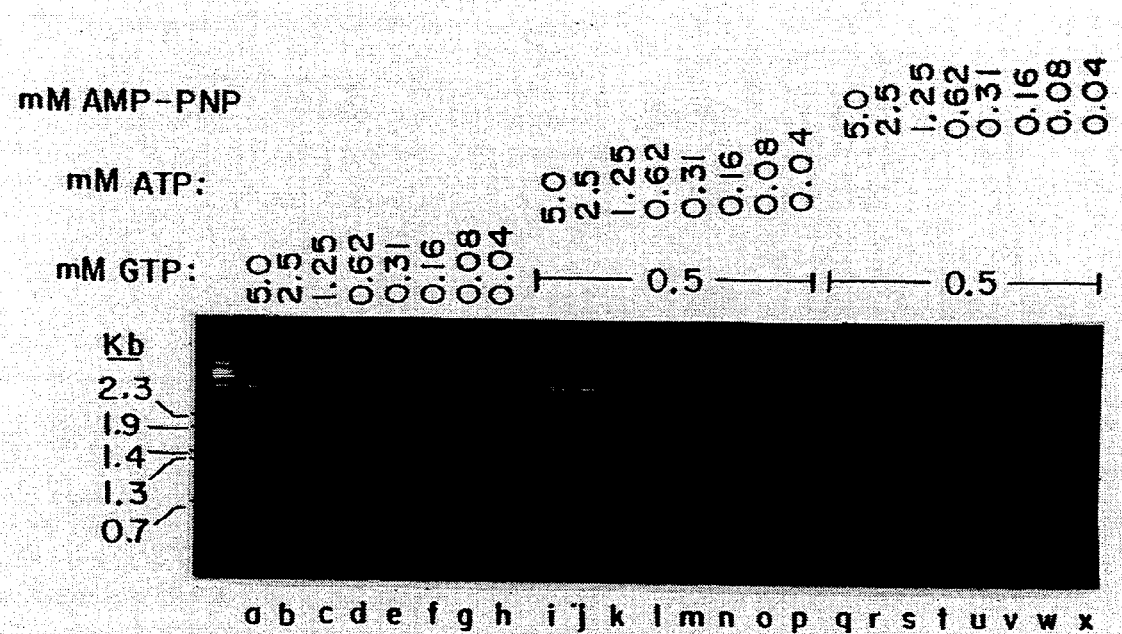
FIG. 2A is a photograph of an agarose gel in which McrBC was used to cleave the substrate pBR322.
Figure 2B:
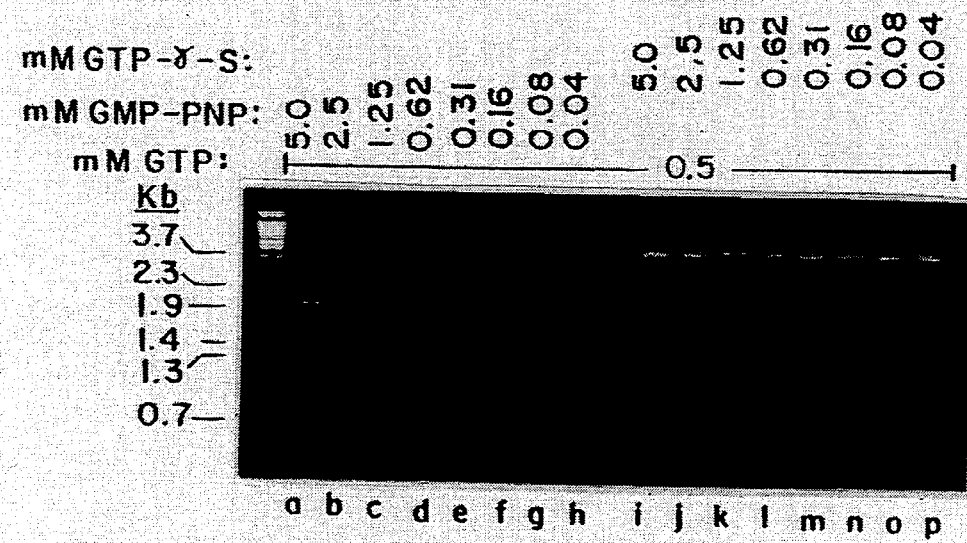
FIG. 2B is a photograph of an agarose gel in which McrBC was used to cleave the substrate pBR322.

The optimal buffer composition for both components of McrBC tested was 10 mM Tris-Cl, 10 mM magnesium chloride, 1 mM GTP (pH 7.5 at 25° C.). As shown in FIG. 2A, relative activity in the same buffer but with 0.62 mM GTP was estimated to be 100%; in the same buffer but with 0.31 mM GTP was estimated to be 50%; in the same buffer but with 0.04 mM GTP was estimated to be 10% or less. FIG. 2A further shows cleavage which was carried out in the presence of varying amounts of GTP (lanes a–h), ranging from 5 mM to 0.04 mM; or in the presence of 0.5 mM GTP and varying amounts of ATP, the ATP concentration ranging from 5.0 mM to 0.04 mM (lanes i–p); or in the presence of 0.5 mM GTP and varying amounts of the non-hydrolyzable ATP analogue, AMP-PNP, the concentration varying from 5.0 mM to 0.04 mM (lanes q–x). FIG. 2B shows cleavage which was carried out in the presence of 0.5 mM GTP and varying amounts of the non-hydrolyzable GTP analog GMP-PNP, the concentration ranging from 5.0 mM to 0.04 mM (lanes a–h); or in the presence of 0.5 mM GTP and varying amounts of the non-hydrolyzable GTP analogue, GTP-gamma-S, the concentration varying from 5.0 mM to 0.04 mM (lanes i–p).

As shown in FIG. 2A, relative activity in the same buffer described above but with 0.5 mM GTP and 0.62 mM ATP was estimated to be 25%; in the same buffer but with 0.5 mM GTP and 1.25 mM ATP was estimated to be less than 10%; in the same buffer but with 0.5 mM GTP and 2.5 mM ATP no activity was detectable (less than 1%). As shown in FIG. 2B, relative activity in the same buffer described above but with 0.5 mM GTP and 1.25 mM GMP-PNP was estimated to be 50%; in the same buffer but with 0.5 mM GTP and 5 mM GMP-PNP was estimated to be less than 10%; no activity was detectable in the same buffer with 0.5 mM GTP when as little as 0.04 mM GTP-gamma-S was also present.

The DNA cleavage reaction herein described is mediated by two proteins, $McrB_L$ and McrC. $McrB_L$ refers to the large polypeptide. McrBC includes the combination of $McrB_L$ and McrC which combination of components is, in accordance with the present invention, substantially free of the third component $McrB_S$. Crude extracts of wild-type cells express a cleavage activity with the properties (position of preferred cleavage, GTP dependence and ATP inhibition) observed for more highly purified preparations (shown in EXAMPLE I) but with very low levels of activity. Further, it was found that the $McrB_L$ complementing activity does not co-chromatograph with the McrC complementing activity when synthesis is directed by a low-copy (pACYC-based) construct expressing both $McrB_L$ and McrC. Therefore, in accordance with one preferred embodiment, overexpressing constructs are provided that direct synthesis of each separately.

One preferred vector for the overexpression of $McrB_L$ and McrC is pAII17, which yields both a low basal level of expression and a high level of induced transcription and at the same time allows replacement of native translation initiation signals with signals known to be used at high efficiency. This vector carries a promoter for T7 RNA polymerase downstream of multiple strong termination signals (to prevent read through transcription from contributing to the basal level of expression) with a lac operator between the promoter and the transcription start point (for the same reason) and LacI constitutively expressed from the same plasmid to prevent loss of regulation.

The McrB translation start used was the second start (nucleotide #18 of the published sequence (Dila et al., J. Bacteriol., 172:4888–4900 (1990)); see FIG. 10 (Seq ID NO:1 and Seq ID NO:2). The McrC start used was the first start (nucleotide 1367). The position of translation initiation was verified by sequencing of the N-terminus of the purified proteins. Attempts were made to purify $McrB_L$ from five different constructs: a low-copy construct in a derivative of the vector pACYC184 with expression directed from the mcrB transcription and translation signals; a moderate-copy construct derived from vector pBR322 with expression directed from the strong lac promoter and mcrB translation signals; a very-high-copy construct derived from the vector pUC19 with expression directed from the strong lac promoter and the mcrB translation signals; and a moderate-copy construct also derived from pBR322 that incorporated a promoter for the T7 RNA polymerase and phage translation signals (described in EXAMPLE I). Although expression as measured by in vitro cleavage activity was increased with the first four constructs, when compared with expression from the single chromosomal copy of mcrB, only the last construct enabled visualization of the $McrB_L$ product on polyacrylamide gels. Purification to near-homogeneity was possible in this last case.

The efficient production and purification of McrB$_L$ seen in EXAMPLE I, from the last construct mentioned, may have resulted from the fact that this construct expresses substantially only McrB$_L$, in contrast with all the other constructs described for which this has been examined. The lack of expression of McrB$_S$ thus appears to be important. This importance is verified by the demonstration that McrB$_S$ acts in vivo to inhibit the restriction activity of a wild-type copy of the operon.

The recognition sequence of the endonuclease of the present invention may be determined by mapping the locations of McrBC cleavage in various DNAs and comparing the DNA sequences of these regions for homology. The McrBC endonuclease was found to cleave pBR322 DNA methylated by M.AluI (AGm5CT) in four principal places.

McrBC was also found to cleave M.AluI-methylated doublestranded pUC19 linearized at the AflIII site to generate fragments of 2.25 kb, 1.9 kb, 1.75 kb, 1.275 kb, 1.15 kb, 1.05 kb 0.94 kb, 0.25 kb and 0.27 kb, consistent with cleavage near nucleotides 250, 2300, 1350 and 325. McrBC also cleaves the following: M.HaeIII-methylated (GGmCC) pUC19 linearized at the AflIII site to generate fragments of 2.25 kb, 1.8 kb, 1.25 kb, 1.05 kb, 0.94 kb, 0.5 kb, and 0.45 kb, consistent with cleavage near nucleotide 1600, 2500, 350 and 550; M.HhaI-methylated (GmCGC) pBR322 near nucleotides 434–494 and near nucleotides 594–548; M.HhaI-methylated pUC19 linearized at the AflIII site to generate bands of 2.25 kb, 1.9 kb, 1.15 kb, and 0.94 kb, consistent with cleavage near nucleotides 0 or 60, 2350, 1500 and 620; M.MspI-modified (mCCGG) pUC19 linearized at the AflIII site to generate bands of 1.6 kb, 1.5 kb, 1.0 kb and 0.9 kb, consistent with cleavage near nucleotides 1500 and 1600. In addition, McrBC degrades the following: M.SssI modified (mCG) pBR322 and M.SssI modified pUC19 DNA; agarose-embedded cellular DNA of Escherichia coli carrying ppvuIIM1.9, which is M.PvuII modified (GAm4CGTC). However, this endonuclease does not degrade Dcm-modified (CmCWGG) pBR322, pUC19 or bacteriophage lambda DNA; M.HpaII-modified (Cm5CGG) pBR322, pUC19, or bacteriophage lambda DNA; and additionally it does not degrade pBR322, pUC19, or bacteriophage lambda modified by both Dcm and M.HpaII.

The sequence Gm5C(N40–N80)Gm5C, which the McrBC endonuclease recognizes, was found to occur in pBR322.

The recognition sequence of the endonuclease of the present invention may be further characterized by cleavage of synthetic oligonucleotides. A doublestranded oligonucleotide containing the McrBC recognition sequence was synthesized—5'GmC(N55)GmC 3': 5'GmC(N55)GmC 3', where methylation is present in both strands. It was found that McrBC cleaved this oligonucleotide. An oligonucleotide containing the same sequence but with methylation of only one strand was synthesized and the McrBC endonuclease cleaved this oligonucleotide as well. Oligonucleotides containing the sequences 5' Cm5C(N55)CmC 3':5'GG(N55)GG 3', 5'Cm5C(N55)Gm5C 3':5'GC(N55)GG 3', and 5'Gm5C(N55)CmC3':5'GG(N55)GC 3', with methylation of only one strand, were synthesized and none of these three oligonucleotides were cleaved. Oligonucleotides containing the sequences 5'Am5C(N55)Am5C3':5'GT(N55)GT3', 5'Am5C(N55)Gm5C3':5'GC(N55)GT3', and 5'Gm5C(N55)Am5C3':5 'GT(N55)GC3' were synthesized, with methylation of only one strand and all three of these oligonucleotides were cleaved. From this evidence it was concluded that McrBC recognizes the sequence Rm5C(N55)Rm5C:GY(N55)GY. From this evidence, taken together with evidence described above, it was concluded that McrBC recognizes the sequence Rm5C(N40–70)Rm5C favorably and the sequence Rm5C(N71–100)Rm5C less favorably, and that the methylation of cytosine need occur only in one strand, and that a cytosine preceding the methylated cytosine at either position in the recognition sequence destroys recognition.

The endonuclease of the present invention may also be characterized by demonstration of cleavage of DNA with modification of cytosine other than m5C. Accordingly, the DNA Escherichia coli W3110(ppvuIIM1.9), which is modified in the sequence CAGCTG at the $N^4$ position of the central cytosine to generate the sequence CAGm4CTG, was treated with. McrBC in the presence of GTP following embedding of the cultured cells in agarose and subsequent lysis in situ to release the DNA, by standard procedures for in situ digestion. DNA carrying this modification was cleaved into many fragments of sizes smaller than 50 kb. From this evidence it was concluded that McrBC recognizes sequences containing $N^4$C. In addition, DNA from bacteriophages T4α gt βgt dam$^h$dam1 and T6αgt, containing 5-hydroxymethylcytosine in place of cytosine and devoid of $N^6$-methyladenine, was first treated with EcoRI or SspI and then treated with McrBC in the presence of GTP. Both of these DNAs were cleaved to produce many fragments smaller than 700 bp. From this evidence it was concluded that McrBC recognizes sequences containing hm5C as well m5C and $N^4$-methylcytosine.

The McrBC endonuclease may be used, therefore, to determine whether an unknown modification resides within the context RmC as well as to locate the approximate position of such modification in relation to the position of cleavage of other restriction endonucleases. The DNA to be examined, which may or may not be radioactively labeled by metabolic incorporation of labeled nucleotide, may be DNA originating from any of a large number of sources. Some of the sources of DNA useful for the purpose of the present invention are: DNA of a natural eubacterial or archebacterial isolate that may express a DNA methylase (Roberts, Nucleic Acids Res., 19:s2077 (1991); Roberts, Nucleic Acids Res., 15:r189–r217 (1989)); DNA of a bacterial strain carrying a cloned DNA fragment or gene from another bacterial strain or species (Wilson, Nucleic Acids Res., 19:2359–2566 (1991)), or from some other organism, for example, the mouse (Bestor et al., J. Mol. Biol., 203:971–983 (1988)) which DNA fragment or gene may encode a DNA methylase; DNA of a virus that may carry DNA modification by virtue of the action of a cellular methylase; DNA of a virus that may carry modification by virtue of a virus-encoded methylase; DNA of a virus that may carry modification by virtue of a virus-encoded enzyme other than a methylase; DNA of a virus that may carry modification by virtue of synthesis of a modified nucleotide and incorporation during biosynthesis of DNA; DNA of intracellular or extracellular virus-like particles; DNA of unicellular eukaryotic organisms; DNA of subcellular fractions of such cells of unicellular organisms; DNA of cells of a plant (Chandler & Walbot, Proc. Natl. Acad. Sci. USA, 83:1767–1771 (1986)); DNA of subcellular fractions of cells of plant origin; DNA of cells of an animal; and DNA of a subcellular fraction of cells of animal origin. In addition, it may be DNA from any of the foregoing sources that has been treated by a modifying activity in vitro (Bloch & Bartos, Current Protocols in Molecular Biology (Ausubel, F.M., et al.), pp 1.3.4–1.3.5, John Wiley and Sons, New York (1991)) which modifying activity may have been isolated from any of the foregoing sources or it may be DNA synthesized in vitro by enzymatic methods or chemical synthesis (Ellington & Green, Current Protocols in Molecular Biology (Ausubel, F.M., et al.), pp. 2.11.1–2.11.18, John Wiley & Sons, New York (1990)).

The DNA from any source may be isolated by an efficient procedure which may be appropriate to the source, including embedding viral particles or virus-like particles or cells or subcellular fractions in agarose or in an alternative matrix which may be devised followed by releasing the DNA in situ. The DNA thus prepared may then be treated by any method of interest which method may be, for example, modification with a methylase or other enzymatic modifying activity from any source. Following such treatment, the samples may be treated with the McrBC endonuclease in the presence of GTP and Mg++. The DNA treated with McrBC may then be fractionated on agarose or polyacrylamide gels or by other means, followed by detection of fragments of interest. Detection may be, for example, by visualization by ethidium bromide staining and photographic imaging, by autoradiography if the DNA was radioactively labelled, or by a Southern blot procedure.

In any of the foregoing procedures, other components enabling cleavage of methylated DNA may be used, which components may specifically recognize and allow cleavage of sequences differently modified than is described above, and such other components may be identified, purified and obtained by one or more processes dependent upon the use of characteristics so far unique to the purified endonuclease described herein. These processes include, for example, 1) examination of cell extracts for endonucleolytic capacity directed against methylated substrates in the presence of GTP as well as Mg++; 2) the production of antibody to purified McrB and/or McrC components described herein, followed by screening cell extracts of natural organisms for the presence of cross-reacting material, followed by testing for the ability of such material cross-reacting with one component to exhibit endonucleolytic activity in a reaction containing material cross-reacting with the other component in the presence of GTP and Mg++; 3) conducting the reactions to test for endonucleolytic activity by any of the processes described in the foregoing four examples at low pH (less than about pH 6.5 and as low as about 5.5); 4) screening cell extracts in the presence of a stimulators factor isolated on the basis of stimulation McrBC cleavage; 5) screening cell extracts of natural organisms for the presence of a component (whether cross-reacting antigenically with either McrB or McrC or not) able to restore endonucleolytic activity to a reaction containing purified McrB or purified McrC but not both, in the presence of GTP and Mg++; 6a) screening of DNA from natural isolates for cross-hybridization to the genes for McrB and McrG, followed by cloning of such DNA into a strain of Escherichia coli devoid of McrBC, or into a strain devoid of both McrBG and Exonuclease V, followed by screening cell extracts from such clones for an endonucleolytic activity directed to methylated DNA and dependent on GTP and Mg++; and 6b) screening of DNA from natural isolates for ability to direct synthesis of an amplified fragment using degenerate oligonucleotides designed on the basis of the polypeptide sequence of the GTP-binding site of McrB that is identifiable due to the demonstration that the McrBC cleavage reaction requires GTP, followed by cloning of such DNA into a strain of Escherichia coli devoid of McrBC, or into a strain devoid of both McrBC and Exonuclease V, followed by screening cell extracts from such clones for an endonucleolytic activity directed to methylated DNA and dependent on GTP and Mg++.

Enzymes related to McrBC$_{K12}$ may be immunologically cross-reactive, especially (but not necessarily) where DNA sequence conservation is sufficient for cross-hybridization to be detected. Cross-reaction to antibody raised with the K12 example may therefore assist in detection of other examples where enzymatic detection is difficult. This may allow partial or complete purification of new examples, sufficient to allow sequence specificity to be characterized. For this to be useful, an immunological method adequate for detection of amounts of protein present in natural sample is needed. Of importance is the ability to obtain enough of the relevant proteins in order to determine the sequence specificity. There are several methods available, described below in EXAMPLE VI, which facilitate the task of purifying the desired proteins in amounts sufficient to determine the nature of the sequence specificity.

The efficiency of the cleavage reaction described herein may be improved by the identification and purification of an additional, as yet unidentified component able to stimulate the endonucleolytic activity of McrBC, which stimulators component may be identified by the use of the purified components of the endonuclease described herein, for example by incubation of cell extracts or chromatographic fractions of cell extracts from Escherichia coli or other enteric species in the presence of GTP with quantities of McrBC or for lengths of time insufficient to allow fragmentation at all identified cleavage sites without the presence of such stimulators component. This may be followed by analysis of cleavage products by agarose or polyacrylamide gel electrophoresis or other suitable fractionation procedure.

The McrBC enzyme is present in very small amounts in wild-type cells, whereas other extraneous nucleases (nonspecific Endonuclease I or analogues, 3'→5' exonuclease Exonuclease III, and nucleotide-dependent Exonuclease V, among others) are present in relatively large amounts. When this is the case, substrates used to detect activity are quickly degraded by the extraneous nucleases and detection is not successful. Successful detection of specific cleavage activity requires either mutant strains defective in one or more of these extraneous nucleases, especially the nucleotide-dependent Exonuclease V (e.g. (Fleishman et al., Proc. Natl. Acad. Sci. USA, 68:2527–2531 (1971)); prepurification of the proteins using an assay other than one for enzymatic activity; or a special condition (low pH) at which the extraneous enzymes are inactive or poorly active. Nuclease-deficient strains can be useful if the genes in question are cloned into E.coli, where nuclease-deficient strains are available.

A productive approach to identifying possible sources of McrBC-like enzymes (in addition to E.coli B) and transforming them to nuclease-deficient K12 strains is to use the mcrBC$_{K12}$ genes themselves to identify the presence of closely related genes in the DNA of candidate organisms. Preliminary unpublished data from Southern blot surveys of a collection of 12 enteric bacteria verifies that cross-hybridizing genes are found frequently, even in such distant relatives as Proteus vulgaris. However, many enteric bacteria including some E.coli species do not contain such cross-hybridizing genes.

Although direct cross-hybridization may be a productive strategy for identifying candidate organisms, for divergent non-cross-hybridizing genes, a probe is needed to identify the likely location of the genes. Candidates for such probes are the conserved intergenic sequence (IGS) and the sequence encoding the GTP-binding site of McrB.

In E. coli, the hsd genes (which encode EcoK, EcoB and EcoA, depending on the strain of origin) are located in the chromosome near to the mcrBC genes. The K and B versions of hsd cross-hybridize, as do the K and B versions of mcrBC; but the K and A versions of hsd do not, even though both exist. However, the intergenic sequence that lies between hsdS and mcrB in K12 and B (the IGS) cross-hybridizes among all three (Daniel et al., J. Bacteriol., 170:1775–1782 (1988)). It may therefore serve as a locator for the position of mcrBC. This may be verified by JK and EAR by Southern blot.

The Choice of oligonucleotides at this location is not constrained by coding requirements and can be chosen from the −500 bp of the intergenic region. Inverted repeats (there are three major ones) and AT-rich regions can be avoided; several different ones will be tried. For example, 23-mer 5'CCCGGATTACAGCCGTATTCCCG3'(Seq ID NO:3) (bp. 1941-63 of published Genbank sequence ECOHSDSK); 27-mer 5'GCGCCGGTTTTGCCACTGGCACGGCGC3'-(Seq ID NO:3) (bp 1993-2020); 30-mer 5'GGTGCAGGCGTTTATTGGAGT-GATTGCCGG3'(Seq ID NO:3) (bp 2141-2170).

The preferred procedure for using such oligonucleotides is to combine them with the GTP-binding site degenerate oligonucleotides and use the PCR procedure to amplify the sequence lying between the two; this should include ∼⅓ of the McrB coding sequence (Triglia et al., Nucleic Acids Res., 16:8186 (1988)). The fragment thus obtained should then be sequenced to verify relationship of the encoded polypeptide with McrB$_{K12}$ and used in Southern blots to identify appropriate fragments for obtaining the complete system.

Ideally two locators are desired for the isolation of mcrBC genes too distant from the K12 instance for cross-hybridization, because this will reduce the chances that genes found are not in fact related to mcrBC. The locator described here (the GTP-binding site) is internal to the McrBC gene. The IGS locator and the GTP-binding site locator can be used together or alone. The locators can be used together using one primer for each locator or each locator can be used alone using two primers from the same sequence and using an inverse PCR procedure.

From comparisons of the amino acid sequences of many many member of the superfamily of GTP-binding proteins, a three-element (Dever et al., Proc. Natl., Acad. Sci. USA, 84:1814–1818 (1987)) or four-element (Bourne et al., Nature, 349:117–126 (1991)) conserved motif was identified. The longest part of the motif was element I: GxxxxGK(S,T), where single-letter amino acid code is used, capital letters represent invariant positions, parentheses surround alternate amino acids at one position, and x indicates that any amino acid may be found among members of the superfamily. McrBC$_{K12}$ requires GTP for cleavage and therefore must bind GTP; in addition, the three elements of the motif identified by Dever were found within the McrBK12 amino acid sequence (Dila et al., J. Bacteriol., 172:4888–4900 (1990)). McrB therefore is a member of this superfamily.

The above described motif can be used to design oligonucleotides for detection and amplification of other sequences encoding this motif. Because the genetic code is degenerate, several different oligonucleotides can encode the same polypeptide sequence; this degeneracy is incorporated into the oligonucleotide design. The family of oligonucleotides to be used is referred to as "the probe".

A 24-mer oligonucleotide with degeneracy of 256 encoding this instance of the element may be designed by choosing G+C-rich codons over A+T-rich codons (in the mcrB instance ⅞ codons end in G or C): 5'GG(G,C)CC(G,C)GG(G,C)GT(G,C) GG(G,C)AA(A,G)AC(G,C)3'(Seq ID NO:6) A backup choice would include A+T rich codons instead:5'GG(A,T)CC(A,T)GG(A,T)GT(A,T)GG(A,T)AA(A,G)AC(A,T)3'(Seq ID NO:7).

The enzyme of the present invention, both components, can also be described in terms of the following properties:

(a) pH optimum: Activity is detectable when the pH of the reaction is lowered to about 5.8.

(b) Optimal ratio of McrB to McrC and of McrC to sites: between one and ten molecules of McrB per molecule of McrC; between one and six molecules of McrC per cleavable site. Higher or lower ratios reduce cleavage activity.

(c) Thermal stability of components in crude extracts of ER1749/pDD41: after incubation of 100 μl of a a crude extract at various temperatures for various times, followed by a 15 minute reaction at 37° C. with 1 mM GTP, the half-life of cleavage activity using pBR322.AluI was approximately 8 hours at 0° C., 8 hours at room temperature (about 25° C.), and approximately 1 hour at 37° C.

The following non-limiting examples further illustrate the embodiments of the present invention.

EXAMPLE I

Purification of McrBC Endonuclease

Purification of the endonuclease took place in two stages, since this endonuclease has two active components; McrB$_L$ and McrC.

A. Purification of McrB$_L$

Figure 3:
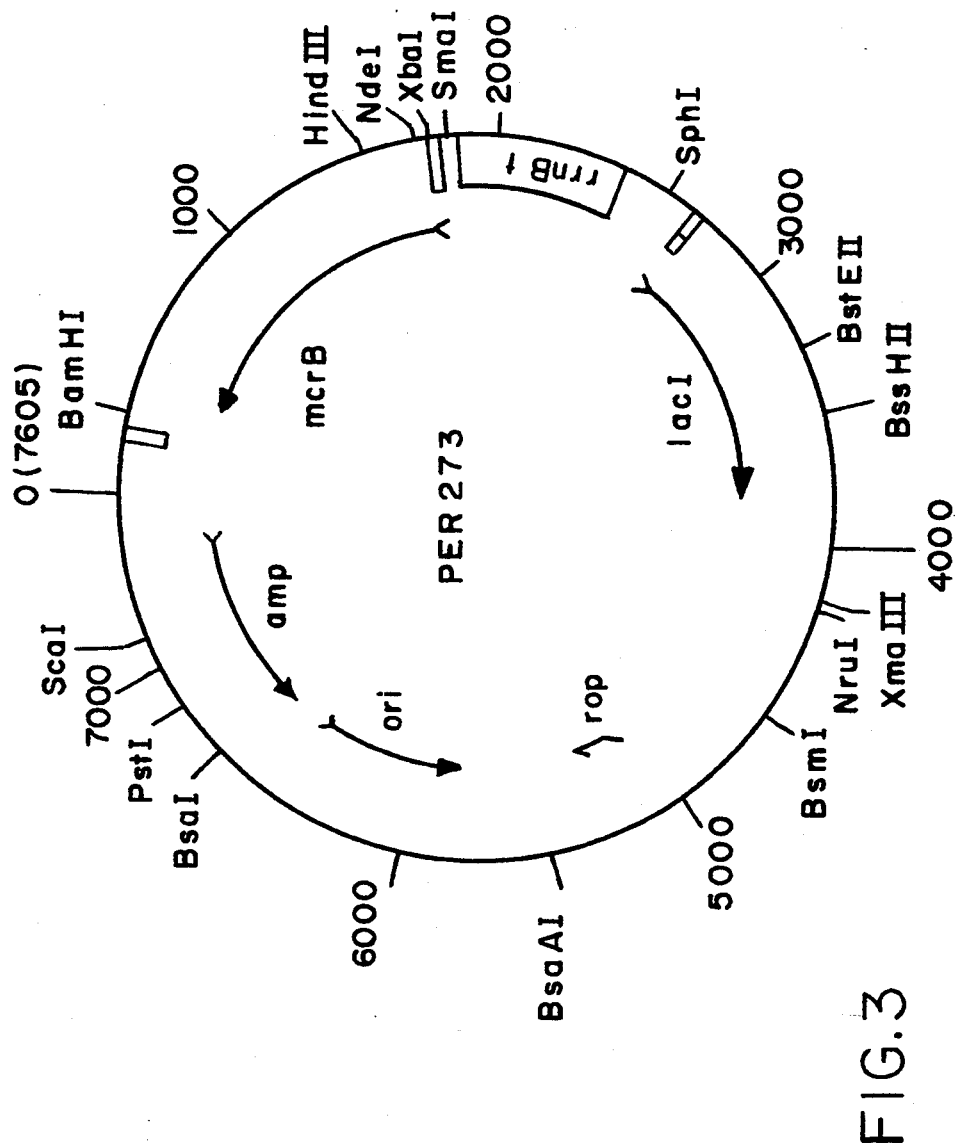
FIG. 3 is a map of the plasmid pER273 which is used to produce the McrB protein.

Escherichia coli strain BL21(DE3)/pER273 was grown in 100 L RBMgAmp media consisting of 10 g/L tryptone, 5 g/L yeast extract, 10 g/L NACl, 1 g/L magnesium chloride hexahydrate, 0.1 g/L ampicillin adjusted to pH 7.2 with 0.3 g/L NaOH. The cells were incubated at 37° C. until late logarithmic stage (149 units read on a Klett-Summerson colorimeter) and induced with IPTG (11.3 g; 0.4 mM final concentration) with aeration and agitation for 1.5 hours. The cells were harvested by centrifugation and stored frozen at −70° C. FIG. 3 shows a map of the plasmid pER273.

Figure 4:
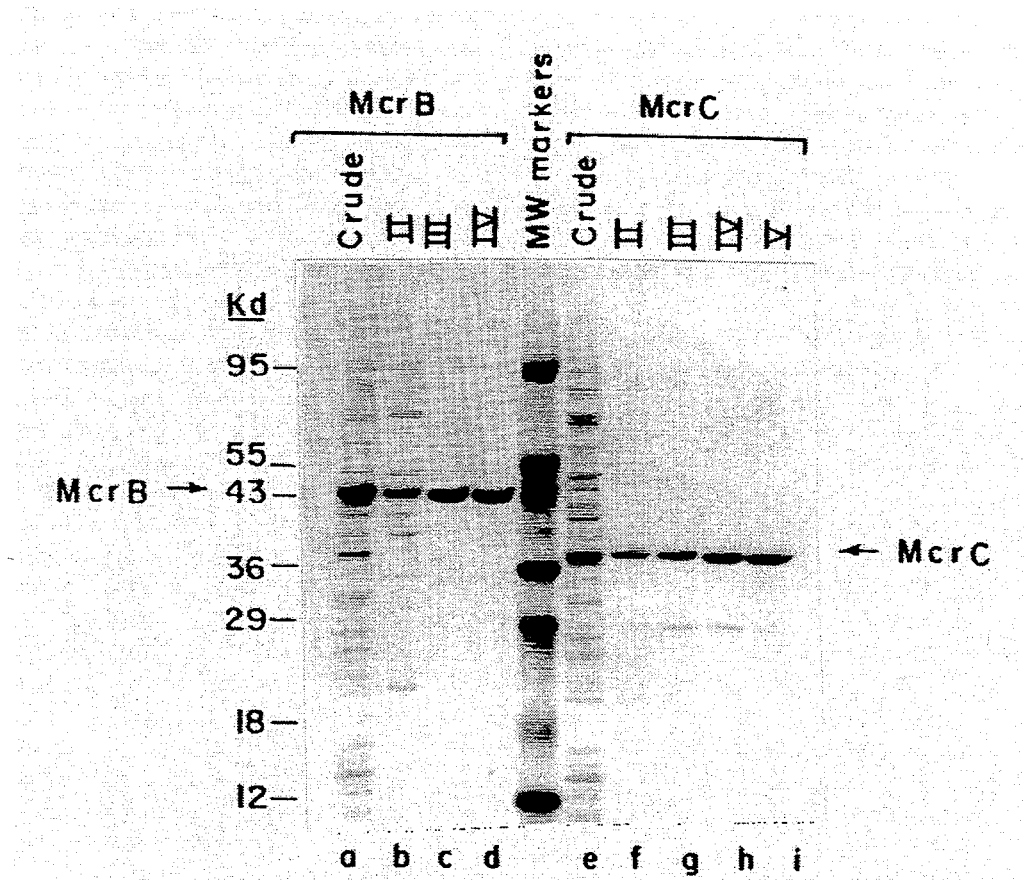
FIG. 4 is a photograph of a polyacrylamide gel in which fractions from the separate purifications of McrB and McrC have been run in the indicated lanes. McrC Fraction V is referred to as Fraction Va in EXAMPLE I.

15 g BL21(DE3)/pER273 were suspended in buffer containing 10 mM Tris.Cl pH 8.0, 50 mM NaCl, 1 mM EGTA, 1 mM EDTA, 1 mM DTT, 25 µg/ml phenylmethylsulfonyl fluoride. Sonic disruption was with three two-minute pulses with a Sonicator TM Cell Disruptor model W-225R with a model H-1 tip (both from Heat Systems-Ultrasonics, Inc., Plainview, N.Y.). Lysis was monitored by measuring protein released into the supernatant of the suspension as detected by the Bradford reagent. Initial protein concentration was 1.68 mg/ml; after the first pulse 6.16 mg/ml; after the third 7.28 mg/ml; after the fourth 6.72 mg/ml. Since there was no further increase in protein concentration after a pulse, cells were judged to be fully lysed. The extract was collected by centrifugation at 12,000 rpm (35 X g ) for 60 minutes at 4° C. This extract was Fraction I. In FIG. 4, which is a photograph of a polyacrylamide gel in which fractions from the separate purifications of McrB$_L$ and McrC have been run in the indicated lanes, Fraction I is in lane a and is designated "Crude".

Fraction I was chromatographed on DEAE Sepharose. 75 ml was loaded onto DEAE Sepharose CL-6B; the column was washed with 300 ml and McrB$_L$ activity eluted during a 0.05-0.5M linear NaCl gradient, at about 0.25M. This activity was monitored using one µl of a 1/20 dilution of a fraction described in part B of EXAMPLE I for each reaction and one µl of a 1/50 dilution of McrB$_L$ column fractions and 0.2 µg of XP12 DNA. From Coomassie-stained SDS-PAGE, the four peak fractions (#40-43) contained 280 mg of protein at the time of collection. About 50% of the protein in the peak fractions precipitated prior to pooling and after incubation at 4° C. Pooled fractions comprising 5% (35 ml) of the gradient volume were clarified by centrifugation and the supernatant (In FIG. 4 Fraction II is in lane b) contained 120 mg of protein as judged by the Bradford reaction.

Fraction II (35 ml) was diluted into buffer containing 10 mM Tris Cl pH7.5, 100 mM NACl, 1 mM EGTA, 1 mM EDTA, 1 mM DTT to a final volume of 105 ml. The diluted fraction was Fraction IIa. Fraction IIa was loaded onto a 25 ml Heparin Sepharose CL-6B (Pharmacia) column. The McrB$_L$ protein and activity eluted during a 0.1-1M NaCl linear gradient at about 0.25M in 10% of the gradient volume (fractions #16-34). This activity was monitored using one µl of a 1/20 dilution of an McrC fraction described in part B of EXAMPLE I, for each reaction and one µl of a 1/50 dilution of fractions from the column. Substrate was XP12 DNA (0.2 µg/reaction). Protein was monitored with Coomassie blue stained SDS-PAGE gels. Fraction #22 of the gradient was designated Fraction III (FIG. 4, lane c). Pooled fractions #18-24 (minus #22) from the gradient were dialysed into phosphocellulose column buffer of 10 mM KPO$_4$, 100 mM NaCl, 1 mM EGTA, 1 mM EDTA, 1 mM DTT, 10% glycerol, pH 6.9 and designated Fraction IIIa.

Fraction IIIa was chromatographed on a 5 ml column of phosphocellulose (Cellulose phosphate P11, Whatman Biosystems, Ltd), washed with 25 ml of column buffer and developed with a gradient of 0.1-1M NaCl. McrB$_L$ activity was recovered in 20 ml of the the flow-through, which was dialyzed into storage buffer (25 mM MOPS, 0.2 mM NaCl, 1 mM EDTA, 1 mM DTT, 20% glycerol, pH 6.5), designated Fraction IV (FIG. 4 lane d) and stored at −20° C. Activity was monitored using one µl of a 1/20 dilution of an McrC fraction, described in part B of EXAMPLE I, for each reaction and one µl of a 1/10 dilution of each fraction from the column and XP12 DNAX(0.2 µg). This fraction was used for experiments determining nucleotide cofactor requirements and oligonucleotide substrate requirements for the reaction, ability of the enzyme to digest agarose-embedded substrate, and ability of the enzyme to digest DNAs modified by various modification methylases and other natural DNAs.

B. Purification of McrC

Figure 5:
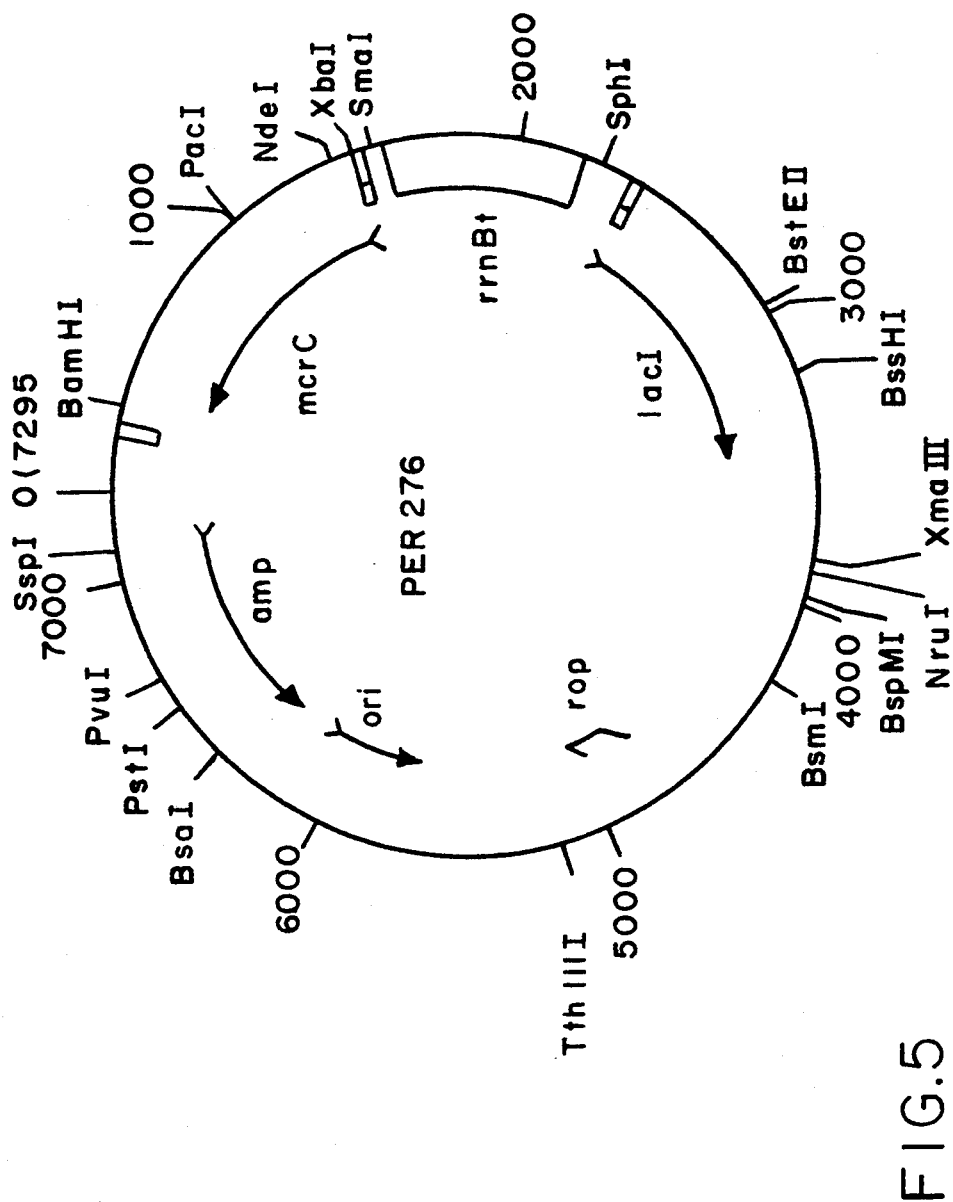
FIG. 5 is a map of the plasmid pER276 which is used to produce the McrC protein.

Escherichia coli strain BL21(DE3)/pER276 was grown in 100 L RBMgAmp media consisting of 10 g/L tryptone, 5 g/L yeast extract, 10 g/L NaCl, 1 g/L magnesium chloride hexahydrate, 0.1 g/L ampicillin adjusted to pH 7.2 with 0.3 g/L NaOH. The cells were incubated at 37° C. until late logarithmic stage (103 units read on a Klett-Summerson colorimeter) and induced with IPTG (11.3 g; 0.4 mM final concentration) with aeration and agitation for 1.5 hours. The cells were harvested by centrifugation and stored frozen at −70° C. FIG. 5 shows a map of the plasmid pER276.

93 g BL21(DE3)/pER276 were thawed on ice in 360 ml of a phosphocellulose column buffer containing 10 mM KPO$_4$ pH 6.9, 200 mM NACl, 0.5 mM EGTA, 1 mM EDTA, 1 mM DTT, 25 µg/ml PMSF. The suspension was subjected to sonic disruption with five two-minute pulses with a Sonicator TM Cell Disruptor model W-225R with a model H-1 tip (both from Heat Systems-Ultrasonics, Inc., Plainview, N.Y.). Lysis was monitored by measuring protein released into the supernatant of the suspension as detected by the Bradford reagent with OD 595 readings. Initial reading was 0.3; after the first pulse, 0.345; after the second pulse 0.40; after the third 0.45; after the fourth 0.47; after the fifth 0.46. Since there was no increase in protein concentration after a pulse, cells were judged to be fully lysed. The crude extract was clarified by centrifugation for 60 minutes at 12,000 rpm in 250 ml bottles and the supernatant designated Fraction I (In FIG. 4, lane e).

360 ml of Fraction I was loaded on a phosphocellulose column (Cellulose phosphate P11, Whatman Biosystems, Ltd), and the column was washed with 400 ml column buffer. The column was developed with a 500×500 ml linear 0.2-1M NaCl gradient at a flow rate of 0.8 ml/minute. Activity was eluted an average concentration of 0.5M NaCl in about 20% of the column volume. Activity was monitored using 1 µl of a 1/100 dilution of a fraction similar to that described in (A) (McrB$_L$ Fraction I) and 1 µl of a 1/200 dilution of the column fractions and 0.2 µg pBR322.AluI. Fractions 48-68 (200-220 ml) were pooled and designated Fraction II (In FIG. 4, lane f).

220 ml of the pooled fractions (Fraction II) were loaded directly on a 50 ml Hydroxylapatite (Calbiochem Corp) column that had previously been de-fined and equilibrated by washing with 300 ml of a buffer of 10 mM KPO$_4$ pH 6.9, 500 mM NaCl, 0.5 mM EGTA, 1 mM EDTA, 1 mM DTT. After loading the column was washed with 250 ml of column buffer and developed with linear 250×250 ml KPO$_4$ gradient (0.01-0.7M), collecting 100 drop fractions (5 ml). McrC activity eluted at an average KPO$_4$ concentration of 0.2M in about 10% of the gradient volume. Activity was monitored using 0..5 µl of a 1/20 dilution of a fraction similar to that described in part A of EXAMPLE I (McrB$_L$ Fraction I) and one µl of a 1/600 dilution of the column fractions and 0.1 mg XP12 DNA. Polypeptide profile was monitored by SDS-PAGE analysis of 2 µl of column fractions and protein concentration was quantitated with the Bradford reagent. Fractions #14–24 were pooled to yield 55 ml, and were diluted 1:2 to a volume of 150 ml (1.5 mg/ml) and dialysed first against 1 liter of a buffer of 10 mM Tris Cl pH 7.5, 150 mM NaCl, 0.5 mM EGTA, 1 mM EDTA and then against one liter of the same buffer but with 200 mM instead of 150 mM NaCl. Approximately 56% of the protein had precipitated during dialysis as judged by the Bradford reagent; the pool was clarified by centrifugation and the supernatant was designated Fraction III (In FIG. 4, lane g).

Fraction III (150 ml) was on loaded onto a 40 ml Heparin Sepharose CL-6B (Pharmacia) column equilibrated with the 200 mM NaCl column buffer described in the previous paragraph, the column was washed with 125 ml of the same buffer, and the column was developed with a 200×200 ml linear gradient of NaCl, collecting 80 drop (4 ml) fractions. Activity was monitored using one microliter of a 1/20 dilution of a fraction similar to that described in part A of EXAMPLE 1 (McrB$_L$ Fraction I) and 1 µl of a 1/500 dilution of the column fractions and 0.1 mg XP12 DNA. Polypeptide profile was monitored by SDS-PAGE, and protein concentration by the Bradford reaction. McrC eluted in 5% of the gradient volume at an NaCl concentration of 0.5M. Fractions 40–45 were pooled to yield 24 ml Fraction IV (In FIG. 4, lane h), which was stored in four five-ml aliquots and one 3 ml aliquot at −70° C.

Five ml (18 mg) of Fraction IV was thawed and diluted slowly 1:4 into a buffer of 10 mM KPO$_4$, 0.1 mM EDTA, 1 mM DTT, 10% glycerol, pH 7.3 to a final concentration of 0.36 mg/ml and loaded onto a Hydropore-SCX column. McrC fractions eluted during a 0–0.5M KCl linear gradient at a concentration of KCl of about 0.2M, in about 5% of the gradient volume. Pooled fractions were dialyzed into storage buffer (25 mM MOPS, 0.2 mM NACl, 1 mM EDTA, 1 mM DTT, 20% glycerol, pH 6.5) and stored at −20° C. (In FIG. 4, Fraction V, lane i).

For a different final step, Fraction IV (5 ml; 18 mg) was thawed and diluted slowly to a final volume of 40 ml into a buffer containing 10 mM Tris pH 8.0, 100 mM NaCl, 1 mM DTT, 1 mM EDTA, 1 mM EGTA, 10% glycerol, dialyzed against 2 liters of the same buffer. A precipitate formed; the suspension was clarified by centrifugation and 35 ml of the supernatant (11.9 mg) was chromatographed on DEAE Sepharose CL-6B. A 5 ml column was loaded with clarified fraction IV, washed with 250 ml of the above buffer and McrC activity was recovered in the flowthrough, which was designated Fraction Va. Activity was monitored using 1 µl of a 1/20 dilution of a fraction similar to that described in Part A (McrB$_L$ Fraction I) and 1 µl of a 1/100 dilution of the column fractions and 0.1 mg XP12 DNA. Polypeptide profile was monitored by SDS-PAGE, and protein concentration by the Bradford reaction. Fraction Va was used in examples II, IV, and VI.

EXAMPLE II

Determination of Recognition Site

A. Cleavage pattern generated by increasing activity on pBR322.AluI linearized at the ClaI site 1. Titering a mixture of McrB$_L$ and McrC. Seven reaction tubes were prepared. The first tube contained 20 µl comprising 3 µl 10 X No-Salt Buffer (100 mM Tris-Cl pH 7.5, 100 mM MgCl$_2$), 3 µl of substrate (pBR322.AluI linearized at the ClaI site; total of 0.3 µg), 3 µl GTP (10 mM at pH 7) and 11 µl dH$_2$O. The other six tubes each contained 20 µl, comprising 2 µl 10 X No-Salt Buffer, 2 µl of the substrate described, 2 µl GTP as described and 14 µl dH$_2$O. 10 µl of a mixture of McrB$_L$ and McrC stored at pH 6.5 at −20° C. was added to the first tube; this was mixed, and 10 µl of the mixture withdrawn and added to the second tube, resulting in a dilution of the enzyme by one-third while retaining a constant concentration of all other components. Similar dilutions were made serially using the remaining five aliquots. Reactions were incubated at 37° C. for 60 minutes and run on 1% agarose gels in TBE buffer. With large amounts of enzyme (tubes 1 and 2), six bands are generated, of about 2.0, 1.6, 0.95, 0.85, 0.7 and 0.6 kb. These are generated from the substrate by cleavage at one or more of three principal sites mapped below (see part B below) and in some cases cleavage at postulated secondary cleavage sites as well. With less enzyme (tubes 3 and 4), cleavage products disappear in a specific order: 0.95, 0.85 and 0.6 kb bands disappear in tube 3; 0.7 and 1.6 kb bands disappear in tube 4, with concomitant appearance of a 2.3 kb cleavage product and a 4.3 kb substrate band. Finally, all cleavage products disappear (tubes 5–7). The positions of modified sites are shown in FIG. 6 which is a diagram of partial cleavage products that could be produced from tile substrate pBR322.

Figure 6:
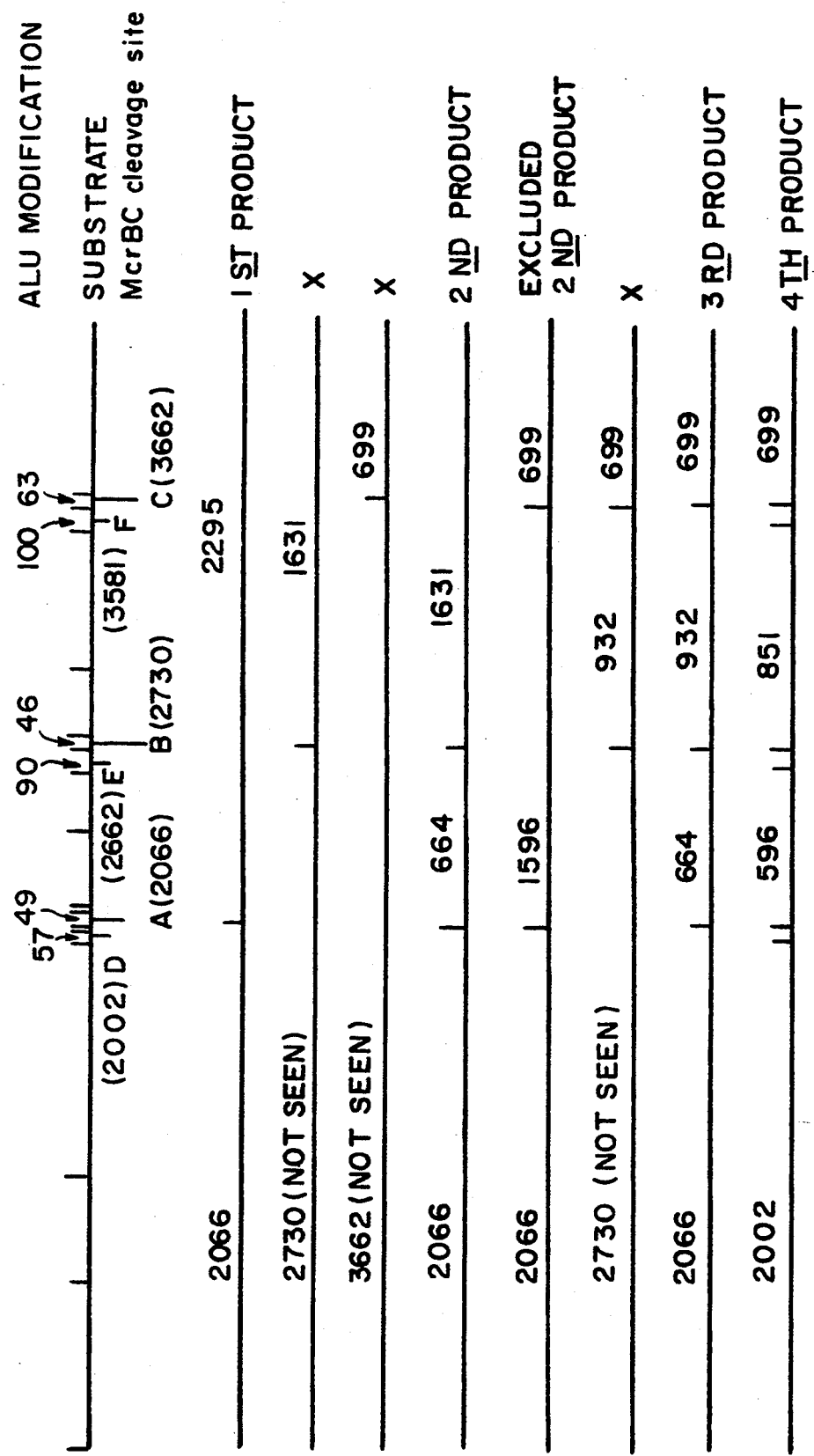
FIG. 6 is a diagram of partial cleavage products that could be produced from the substrate shown in FIG. 1 if all sites were cleaved with equal efficiency.

In FIG. 6, the substrate is redrawn at the top, with the three principal cleavage sites (A–C) indicated as in FIG. 1 and three possible secondary cleavage sites (D–F) also indicated. Site D has been shown to be cleaved (EXAMPLE III and FIG. 7); sites E and F have not been conclusively identified. Partial cleavage products appear in the order given, and some products do not appear (X). The cleavage sites shown in FIG. 6 were determined from this analysis together with the mapping experiment described in part B below.

B. Mapping McrBC-cleaved pBR322.AluI relative to various endonuclease cleavage sites pBR322 was modified by M.AluI by standard methods, cleaved with ClaI, and resuspended at 0.1 µg/µl. This substrate was recleaved with one of four restriction endonucleases that cleave once in pBR322 (AflIII, NdeI, ScaI, or SspI). These reactions (0.4 µg DNA in each, cleaved in a volume of 20 µl with the appropriate buffer supplied by New England Biolabs) were phenol extracted, precipitated by addition of ethanol in the presence of salt, and resuspended in dH$_2$O. Half of each reaction (0.2 µg) was digested with McrBC (1 µl each of McrB$_L$ and McrC; McrB$_L$ was similar to McrB$_L$ fraction iii of EXAMPLE III; McrC was similar to McrC fraction ii of EXAMPLE III). Reactions were loaded onto an agarose gel, with size standards (pBR322 digested with BstNI; NEB #301-1) and the sizes of the various fragments determined from a log-linear plot of cm migration (from a Polaroid photograph) versus known size of size standards. Sizes of fragments larger than the largest size standard were estimated by extrapolation and are indicated by "~". Sizes were lane 1, size standard: 1857, 1060, 929, 383, 121 bp; lane 2, AflIII+McrBC: >4 kb (faint, partial digest product), ~2.5, ~2.2, 1.7, 0.7 kb; lane 3, AflIII: ~2.6, ~2.1 (expected sizes 2.449, 1.912); lane 4, NdeI+McrBC: ~2.2, ~2.1, 1.8, 0.4 kb; lane 5, NdeI: ~2.5, ~2.2 kb (expected sizes 2.272, 2.089); lane 6, McrBC: ~2.2, 1.7, 0.93, 0.66, 0.48 kb; lane 7, ScaI: ~3.7, 0.54 (expected sizes 3.822, 0.541); lane 8, ScaI+McrBC: ~2.1, ~1.9, 1.1, 0.66, 0.60, 0.54 kb; lane 9, SspI: ~3.7, 0.28 kb (expected sizes 4.146, 0.215); lane 10, SspI+McrBC: ~2.2, 1.35, 0.66, 0.56 kb. This information, taken together with the information in part A suggesting ordered cleavage, enabled us to determine the positions of principal McrBC cleavage sites and probable locations of secondary cleavage sites (See FIG. 6).

C. Determination of cleavage patterns on pUC19 methylated by M.AluI. M.HaeIII, M.HhaI, M.MspI and failure to cleave M.HpaII DNA used was pUC19 linearized at the AflIII site, obtained by standard procedures, and then methylated (0.8 μg) in a reaction containing 8 μl 10 X buffer (for M.AluI, M.HhaI, and M.HpaII this was 10XM.FnuDII buffer: 500 mM Tris[Cl] pH 7.5, 100 mM EDTA, 50 mM β-mercaptoethanol; for M.HaeIII, 500 mM Tris [Cl] pH 8.5; 500 mM NaCl, 10 mM dithiothreitol; for M.MspI, 500 mM Tris, pH 7.5, 500 mM NaCl, 50 mM β-mercaptoethanol; for M.SssI, 500 mM Tris Cl, pH 8.0, 500 mM NaCl, 100 mM EDTA), 8 μl S-adenosylmethionine (32 mM in 5 mM $H_2SO_4$, 10% ethanol) and 4 μl methylase (M.AluI, 5 units/μl; M.HaeIII, 5 units/μl; M.HhaI, 25 units/μl; M.HpaII, 1-5 units/μl, M.MspI, 5 units/μl, M.SssI, 2 units/μl) in a total volume of 82 μl. Methylation reactions were incubated 90 minutes at 37° C., then heat-killed by incubation for 15 minutes at 67°-70° C. These substrates were then distributed to 6 series of 7 tubes for McrBC titration. The first tube in each series contained 20 μl of the respective methylated DNA, 4 μl 10X No-Salt Buffer, 4 μl 10 mM GTP, 0.4 μl 1M $MgCl_2$, and 2 μl $H_2O$; the remaining tubes in each series contained 10 μl of the respective methylated DNA, 2 μl 10 X No-Salt Buffer, 2 μl 10 mM GTP, 0.2 μl 1M $MgCl_2$, and 6 μl $H_2O$. Reaction was begun by addition of 10 μl of McrBC (a 1:1 mixture of $McrB_L$ (Fraction III of EXAMPLE I) and McrC (a 1:5 dilution of Fraction Va of EXAMPLE I)) to the first tube of each series, followed by serial dilutions of 20 μl from each tube to the next.

These samples were run on an agarose gel with size standards (lambda digested with BstEII-New England Biolabs (NEB) 301-4) and fragment sizes determined as in part B. With this preparation of McrBC, the limit digest fragment sizes for the M.AluI-methylated substrate were 1.275, 1.15, 1.05, 0.94 and ~0.34 kb. Since these add up to more than the size of pUG19 (2.686 kb), these must result from incomplete digestion. Additional partial digest products visible with less enzyme were 1.75, 1.9 and 2.25 kb and ~0.44. These are consistent with ordered cleavage in the vicinity of bp 250, 2300, 90, and 1300. The limit digest fragment sizes for the M.HaeIII-methylated substrate were 1.25, 1.05, 0.94, 0.5 and 0.45 kb. Additional partial digest products visible with less enzyme were 1.8, 2.25 and 2.4 kb. These are consistent with ordered cleavage in the vicinity of bp 1600, 350, and 550. The limit digest fragment sizes for M.HhaI, and M.MspI-methylated substrates could not be easily distinguished, but defined bands were visualized with small amounts of enzyme. For M.HhaI: 2.4, 2.25, 1.9, 1.15, 0.94 kb, consistent with cleavage in the vicinity of 0 or 60, 2350, 1500 and 630 for M.MspI: 1.6, 1.55, 1.0 and 0.9 kb, consistent with cleavage in the vicinity of bp 1500 and 1400. For M.SssI, extensive degradation was seen, and therefore specific bands could not be correlated with cleavage at specific sites.

Favored cleavage sites identified above correspond with sequences in which the sequence $Rm5C(N_Y)Rm5C$ appears, with Y=40-80 (Table I, strong sites) and weaker cleavage sites with Y=80-111 (Table I, weak sites). One weak site appears to correspond with Y=297. Two strongly favored sites (site A for pBR322.AluI-ClaI, and the site at ~250 on pUC19.AluI-AflIII) may result from cleavage at two overlapping sites that fit the model. No sequences were found that both fit the model for strong sites and were not cleaved. Seven sequences were found that fit the model for weak sites but which could not be assessed as targets with the methods used because they were too close to strong sites or to the ends of the linear molecule. DNA modified in such a way that the $R^mC$ motif could not be created (modified by Dcm ($C^mCWGG$) or by Dcm and M.HpaII ($C^mCGG$)) was not cleaved at all.

Four sequences were found that could be ruled out as cleavage sites, with Y=11, 19, 19 and 21 (two of these were ruled out by methods described below, see EXAMPLE III). Three additional sequences with Y=11, 19 and 21 were probably not cleaved but cleavage could not; be ruled out with the methods used.

EXAMPLE III

Determination of the McrBC Cleavage Site

This determination took place in three stages: isolation of the $McrB_L$ and McrC proteins and a primer-extension experiment for characterization of cleavage position.

A. Purification of $McrB_L$ 5.21 g ER1945/pDD48 were suspended in 10.4 ml EB (50 mM Tris[Cl] pH 7.5, 50 mM NaCl, 10 mM $MgCl_2$, 25 μg/ml phenylmethylsulfonyl flouride, (PMSF; Calbiochem)) and were lysed with lysozyme (20 μl lysozyme (10 mg/ml) per ml of cell suspension; 300 μl) and NaCl to a final concentration of 40 mM (150 μl of 4M). The mixture was vortexed and incubated on ice for 20 minutes. Lysis was Judged by increase in viscosity due to release of chromosomal DNA.

Fraction i was prepared by lysis similar to that in the previous paragraph of cells in a total volume of 25 ml, then clarifying the lysed mixture by low-speed (35 X g for 60 min at 4° C.) and high-speed (110 X g for 30 min at 4° C.) centrifugation. Fraction i was stored at −70° C.

Fraction i (25 ml) was loaded on a 20 ml phosphocellulose column; $McrB_L$ activity recovered in the flow-through (20 ml) and designated Fraction ii. This activity was monitored using 1 μl of an McrC fraction similar to that described in part B of EXAMPLE III (McrC purification #1, fraction ii) for each reaction and five serial five-fold dilutions of $McrB_L$ column fractions, beginning with four μl per reaction.

10 ml of Fraction it was dialyzed into 10 mM Tris[Cl] 100 mM NaCl, 1 mM DTT, 1 mM EDTA, pH 7.5 and 5 ml of the dialysate chromatographed on Heparin Sepharose. The column (3 ml) was washed with 10 ml of Tris pH 8.0, DTT, 0.1M NaCl and developed with a 15 ml linear gradient of 0.1-1.0M NaCl, collecting 15 drop fractions. $McrB_L$ was recovered, in the wash volume and designated Fraction iii. This activity was monitored using one μl of an McrC fraction similar to that described in EXAMPLE III (McrC purification #1, fraction ii) for each reaction and one μl of $McrB_L$ column fractions. Fraction iii was stored in 100 ml aliquots at −70° C.

B. Purification of McrC 8.7 g of ER1945/pPB2 was suspended 17.4 ml of EB (50 mM Tris[Cl] pH7.5, 50 mM NaCl, 10 mM MgCl$_2$, 25 μg/ml phenylmethylsulfonyl flouride, PMSF(Calbiochem) to a total volume 25 ml). 500 ml lysozyme (10 mg/ml) and 250 μl 4M NaCl were added, cells were vortexed and incubated on ice for 20 min, and lysis was monitored by an increase in viscosity of the suspension. The lysed mixture was centrifuged 60 min at 16,000 rpm, and the supernatant (17.5 ml) was filtered through Millex 0.45 micron low-protein-binding filter to yield 15 ml of Fraction i.

Heparin Sepharose CL-6B (Pharmacia; 15 ml) was regenerated by washing with 6M urea, 3M NaCl and column buffer (10 mM Tris [Cl] pH7.5, 100 mM NACl, 1 mM EGTA, 1 mM EDTA, 1 mM DTT). 15 ml of Fraction i was loaded on a 15 ml column of this Heparin Sepharose, washed with 30 ml of column buffer and eluted during a 75×75 ml 0.1–1M NaCl linear gradient collecting 24 drop fractions. The gradient was interrupted part way through and the column was eluted with 15 ml 0.5M NaCl. Activity eluted at a concentration of about 0.5M. Activity was monitored using one μl of a fraction similar to that described in Part A EXAMPLE III (fraction iii McrB$_L$) and 0.2 μg of the pBR322.AluI substrate shown in FIG. 1. Fractions 45–60 were pooled to yield Fraction ii.

Fraction ii was dialyzed into a buffer containing 10 mM KPO$_4$, 0.2M NaCl,1 mM DTT, 1 mM EDTA, pH 6.9 and 5 ml loaded on to a 2.5 ml phosphocellulose column (Cellulose phosphate P11, Whatman Biosystems, Ltd). The column was washed with 5 ml of the same buffer and the McrC activity eluted during a 10×10 ml linear KPO$_4$ gradient (0.01–0.7M) at a concentration of about 0.3M. 9 drop fractions were collected into tubes containing 4 μl BSA (10 mg/ml). Activity was monitored using two microliters of McrB$_L$ fraction iii described in EXAMPLE I and one microliter of column fractions and 0.2 μg of pBR322.AluI. Fraction #26 was designated Fraction iiia. Pooled fractions #24–30 were 4 ml, designated Fraction iii and were stored in 100 μl aliquots at −70° C.

C. Primer extension

Sequencing reactions were performed to allow alignment of cleavage sites with the sequence of the region cleaved. Oligonucleotide primers for both sequencing and primer extension were end-labelled by incubation with gamma-[$^{32}$P] ATP and T4 polynucleotide kinase for 30 min at 37° C. Templates for DNA sequencing were CsCl-purified plasmid DNA denatured by incubation in a 0.2M NAOH solution for 15 min at 37° C., followed by ethanol precipitation. Dideoxy DNA sequencing (Sanger et al., J. Mol. Biol., 143:161–178 (1980)) used a collapsed-plasmid protocol, (Hattori and Sakaki, Anal. Biochem., 152:232–238 (1986)).

The position of cleavage by McrBC was determined by extension of primers annealed to precleaved substrate (Hattori and Sakaki, 1986). Unmodified supercoiled pBR322 or pBR322.AluI was prepared as described above but not linearized. Cleavage with McrBC, DrdI, HinfI, PvuII, or a combination, was carried out using one μg substrate in a total volume of 30 μl. McrBC was used as 3 μl McrB$_L$ fraction iii, 3 μl McrC fraction iii. Digestions were carried out serially.

For detection of cleavages, the cleaved substrate was extracted with phenol/chloroform, precipitated with 0.75 volume of isopropanol, resuspended in TE (10 mM Tris[Cl], 1 mM EDTA, pH 7.5). Five to seven pmole of primer was added to one pmol of template DNA in a final volume of 10 μl, the mixture was denatured by boiling for five min using a heating block and annealed by removing the block from the heating surface to cool. Extension reactions included, in addition to template and primer as described, 250 mM each dATP, dGTP, dCTP and dTTP in sequencing buffer (10 mM Tris[Cl], pH 7.5, 5 mM MgCl$_2$, 7.5 mM dithiothreitol) and five units Klenow fragment in a final volume of 30 μl and were carried out for 20 min at 37° C. Reactions were stopped with 6 μl STOP dye (NEB #428), and the products were analyzed on 8% polyacrylamide-urea gels. Gels were fixed, dried and autoradiographed according to Tabor (Tabor, 1988) using Kodak XAR-5 X-ray film, with exposure at room temperature.

This experiment showed cleavage of site A shown in FIGS. 1 and 6. This strongly preferred McrBC cleavage site is found in a cluster of five AluI sites within 140 basepairs. Any or all of the ten modified cytosines associated with these AluI sites could be required for recognition or cleavage.

The primers used had 3' ends annealed at bp 1969 (top strand) or bp 2228 of pBR322. Within this region sites for control restriction cleavage were also found. HinfI cleaves at 2031 to yield a three-base 5' extension, PvuII cleaves at 2066 to yield a blunt end, and DrdI cleaves at 2164 to yield a five-base 3' extension. These reactions resulted in the synthesis of labelled DNA complementary to one cut strand of pBR322 DNA, of a length determined by the position of the cleavage. Results are shown in FIGS. 7A and B.

Figure 7A:
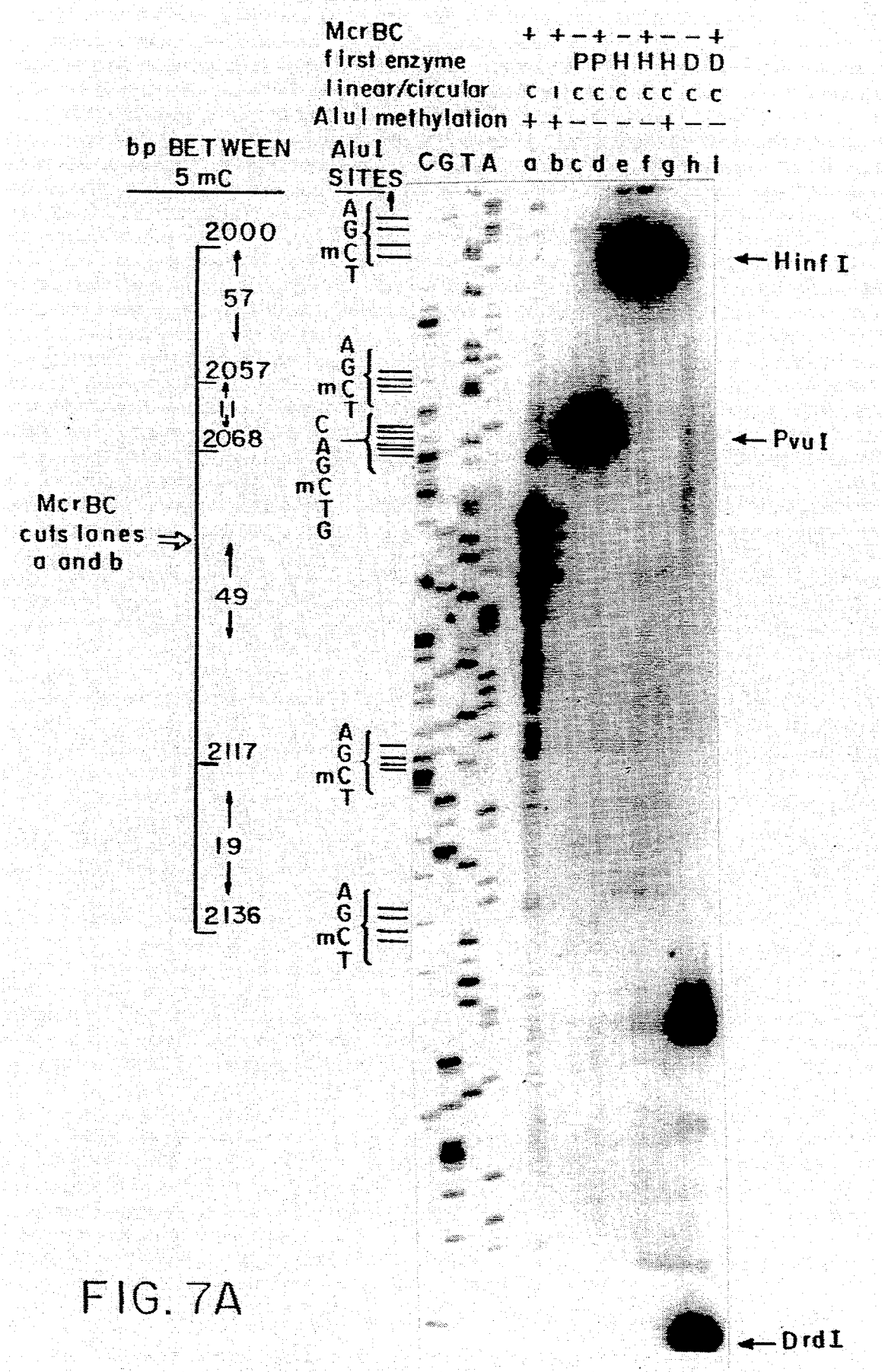
FIG. 7A is a photograph of an autoradiogram of a polyacrylamide gel used for determination of the sites (A and D in FIG. 1) at which McrBC cleaves pBR322 methylated with M.AluI.

FIGS. 7A and B are photographs of an autoradiogram of a polyacrylamide gel used for determination of the sites (A and D in FIG. 1 at which McrBC cleaves pBR3222 methylated with m.AluI in the region between 2000 and 2138 (sequence numbered as in Genbank 1988). The sequencing lanes (labelled C, G, A, T) were generated by standard dideoxynucleotide sequencing reactions on supercoiled pBR322. Lanes in which McrBC cleavage is shown (lanes (a) and (b) in both FIG. 7A and 7B) contain samples in which either pBR322 DNA was methylated with m.AluI and then cleaved with McrBC (lanes a), or it was cleaved with ClaI and then methylated with m.AluI and then cleaved with McrBC (lanes b); in both cases the cleaved product was then used as substrate for primer extension reactions. $^{32}$P-labelled primers were identical to the bottom strand from bp 5' 2255-2229 3' (revealing cleavage of the top strand, FIG. 7A) or to the top strand from bp 1942-1968 (revealing cleavage of the bottom strand, FIG. 7B). In other reactions unmethylated DNA was cleaved with PvuII (lane c), or with PvuII and McrBC (lane d) or with HinfI (lane e) or with HinfI and McrBC (lane f), or m.AluI-methylated DNA was cleaved with HinfI (g), or unmethylated DNA was cleaved with DrdI (lane h) or with DrdI and McrBC (lane i).

Figure 7B:
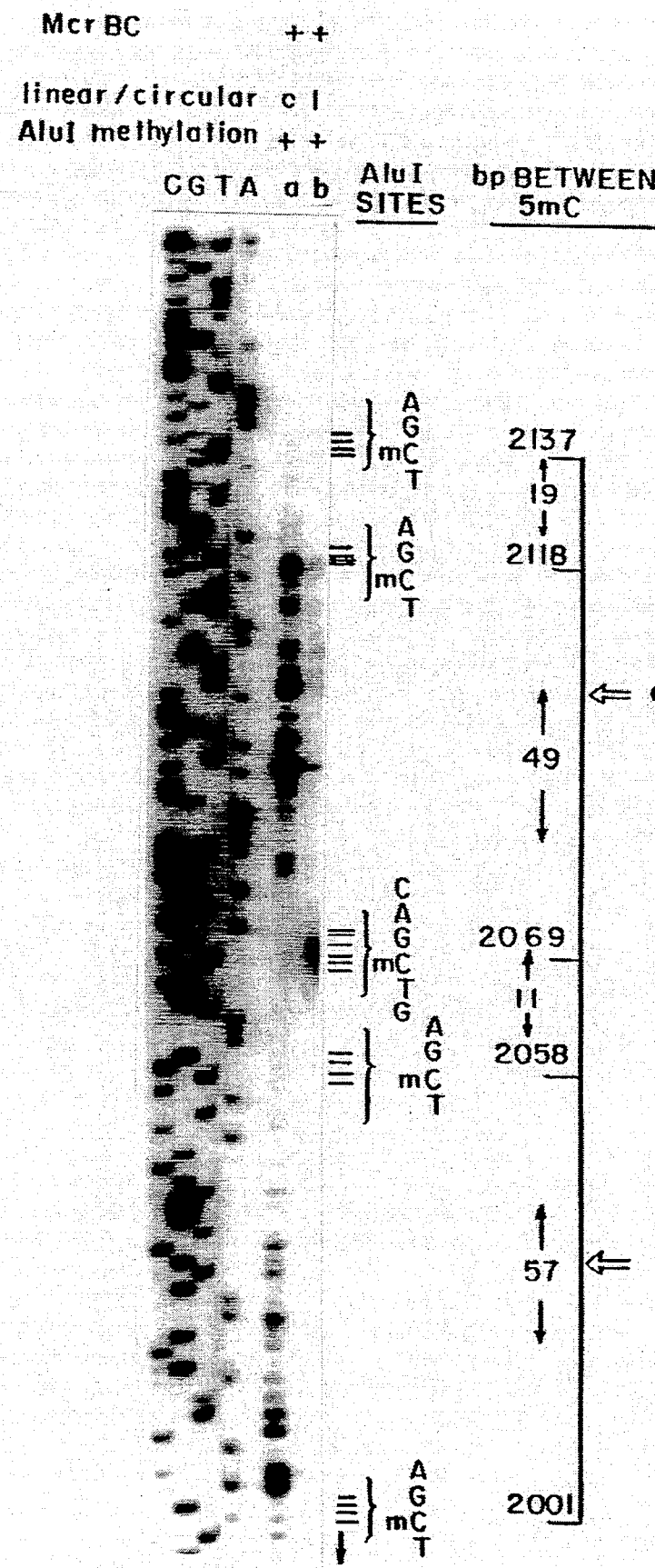
FIG. 7B is a photograph of an autoradiogram of a polyacrylamide gel used for determination of the sites (A and D in FIG. 1) at which McrBC cleaves pBR322 methylated with M.AluI.

In FIGS. 7A and B, sequencing reactions generate fragments of lengths determined by the sequence of the primed strand rather than the sequence of the opposite strand, whereas the cleavage reactions generate fragments of lengths determined by the position of cleavage on the opposite strand. For clarity, therefore, the sequence lanes are labeled to reflect the sequence of the opposite strand (reactions containing ddGTP are labled C, etc). For simplification of the figure and clarity of the results, the sequences in FIGS. 7A and B have been labelled to reflect the sequence of the cleaved strand rather than its synthesized complement. Accordingly, the sequence reads 5'→3' from top to bottom rather than the reverse. McrBC cleavage of closed circular and linear modified DNA is shown in lanes (a) and (b) respectively in each panel; FIG. 7A shows cleavages made on the top strand of pBR322 as conventionally represented and FIG. 7B shows those on the bottom strand. The most striking fact about these lanes was the large number of product bands present. These bands resulted from the intrinsic action of McrBC, not from contaminating nuclease, as discussed below.

Controls designed to detect nuclease contamination of the McrB$_L$, McrC or m.AluI methylase preparations, or other artifactual results, included cleavage with PvuII (P), HinfI (H) or DrdI (D). Unmodified plasmid DNA was cleaved with one of these, the sample was divided, one aliquot was treated with McrBG, and both aliquots were analysed. Band patterns in each pair of lanes (FIGS. 7A and B, lanes c–d, e–f and h–i) were identical, so no exonuclease contaminated the McrB$_L$ or McrC fractions. Similarly, nonspecific single or double-strand endonuclease contamination of the m.AluI methylase preparation was ruled out by cleaving modified plasmid with HinfI (lane g). A comparison of lanes (e), (f), and (g) shows no products derived from the methylated DNA not found in the unmethylated DNA.

Isolated, intensely labeled bands were obtained from digests with conventional restriction enzymes (FIGS. 7A and B, lanes c–i), which are known to cleave a single phosphodiester bond on each strand, at a position found in a defined relationship to the recognition site. Accordingly the multiple band pattern obtained from McrBC digestion strongly indicates that McrBC cleavage occurred at multiple sites with a looser relationship to the recognition site. However, we are reluctant to draw firm conclusions about the precise position of the the cleavages. Two potential artifacts for which we cannot completely control concern us. One results from secondary priming sites. Such a site, as shown in FIG. 7A, lanes h and i, is clearly present in the DrdI-cleaved control. The position of the DrdI cleavage in the region of interest is indicated (bottom right of the panel). The dark band above the known cut site is most likely due to a secondary priming site identified close to the only other DrdI site on pBR322, at position 2577. Priming the extension reaction from this site should not add extraneous bands to the McrBC lanes, since no mapped McrBC sites are in the vicinity of this position and any such product would not enter the gel. Other possible secondary priming sites that might interfere have been identified, but clearly there are not as many such sites as there are bands in lanes (b). Secondary priming sites would not necessarily interfere with the DNA sequencing reaction to the left in FIGS. 7A and B, because these reactions use collapsed supercoiled plasmid templates and therefore required a three-fold lower concentration of primer than the linear template used in the experimental reactions. The lower primer concentration should minimize secondary priming.

The second potential artifact can result in the appearance of pairs or triplets of bands where there should be only one. The cause of this "stuttering" is slippage of the Klenow polymerase near the end of DNA fragments, particularly in AT-rich regions. Melting of the ends followed by reannealing out of register may allow addition of an extra base (often a T); or exonucleolytic attack on melted (apparently mismatched) terminal bases may remove a base. This particular artifact was seen with HinfI digestion in some experiments. Its possible contribution to the pattern in lanes (a) and (b) is difficult to assess. However, the experiment shown in FIGS. 7A and B was repeated four times using different DNA preparations and at least three different preparations each of McrB$_L$ and McrC. In all cases, the banding pattern was essentially identical.

The multiplicity of cleavage products in lanes (a) and (b) of FIGS. 7A and B is therefore intrinsic to the McrBC enzyme. Such a multiplicity might result if McrBC bound in a different particular alignment to the DNA sequence when the topology differed-i.e., each of the different topoisomers that are found in natural preparations of covalently closed circular DNA (lanes a) might be cleaved differently. Accordingly, we analysed the products of reaction with linear DNA (lane b of FIGS. 7A and B), which should be topologically uniform. The band pattern is not detectably altered, although in this experiment the bands in the linear sample are lighter due to a lower starting DNA concentration. This particular model for generation of different cleavage positions was therefore eliminated.

Although there are apparently numerous cleavage sites, these are restricted to positions between two methylated sites (FIGS. 7A and B). The positions of methylated AluI sites, and the distance between methylated base (this distance is mC(1)-mC(2) in the terminology of Table I above), are indicated to the left in FIG. 7A and to the right in FIG. 7B. The cleaved sites appeared between methylated bases 49 bp apart on the top strand (bases indicated at 2068 and 2117 in FIG. 7A) and between the same two sites on the bottom strand (bases at 2069 and 2118 in FIG. 7B). These cleavages correspond to site A in FIG. 1 where pBR322.AluI is shown linearized at the ClaI site (horizontal line), with the positions of the methylated AluI sites (vertical ticks above the line) and the positions of cleavage of the DNA by McrBC (vertical arrows below the line) indicated. In FIG. 7B, cleavage also occurred between bases 57 bp apart (2001 and 2058); these correspond to site D in FIG. 1, as discussed below. However, no cleavage products migrated between the methylated bases 11 bp apart (2057 and 2068), or 19 bp apart (2117 and 2136) in the top strand in FIG. 7A or in the corresponding position on the bottom strand in FIG. 7B.

These experiments are consistent with the mapping experiments described in EXAMPLE II. The model of a site (RmC(N$_{40-80}$)RmC) could be further confirmed as follows. First, the cluster of cleavages between methylated bases 49 base pairs apart ((mC(2)−mC(1)−1)=N$_\gamma$=48) could also be said to occur between bases 60 bp apart (N=59); that is, between 2057 and 2117 rather than between 2068 and 2117. We propose that two cleavage sites are superimposed here. This "double site" (site A) with 48 and 59 bp spacing is closer to the primer in FIG. 7A than is the "missing" 56-base single site (site D), but further away from the primer in FIG. 7B. Thus, some molecules of plasmid might be cleaved at site D, yielding short products in FIG. 7B but long products in FIG. 7A. But possibly, all molecules would be cleaved at site A (the "double site"), yielding long products in FIG. 7B but truncating the long products in FIG. 7A to short ones. The top strand long products would thus be missing from the gel.

A partial test of the "double site" model was carried out by disrupting the AluI site at 2068. This was accomplished by inserting an 8 basepair MluI linker at the PvuII site, which contains the 2068 AluI site. When methylated by M.AluI, only a "single" McrBC site at site A should be created, with 67 base pairs between methylated cytosines (those at positions 2117+8 and at 2057). A pattern of multiple bands was obtained similar to, but not identical with that shown in FIG. 7 (data not shown). This confirmed that the methylation site at 2068 was not necessary for cleavage. Cleavage of a substrate carrying the site at 2068 but not 2057 (see EXAMPLE IV) verified that the converse was also true.

EXAMPLE IV

Cleavage of Synthetic Oliogonucleotides Containing $m^5C$

Twenty-four 82-basepair synthetic oligonucleotide duplexes were used as substrates for McrBC cleavage.

The sequence of these was based on the sequence of pBR322 (bp 2056-2137 inclusive) around the cleavage site shown in FIGS. 7A and B, except that in all of them the AluI site at bp 2058 was eliminated by changing the C to a G. The sequence of the top strands is shown in Table II (Seq ID NO:8) below. In seven of the duplexes the two AluI sites that flank the cleaved positions in FIGS. 7A and B are retained (underlined in Table II Seq ID NO:8)). The ) oligonucleotides were synthesized with m5C (represented as M in Table II (Seq ID NO:8)) at one, both, or neither AluI recognition sequence in each strand. A HinPI site near the left end of the duplex (boxed in Table II (Seq ID NO:8)), could be cleaved with HinPI to yield a large and a small fragment, each bearing a single AluI site. This enabled us to create two additional doublestranded oligonucleotides. Results for all of the configurations of methyl groups, as well as for the single strand, are shown in the first column of Table III below, rows 1–12.

TABLE II

```
AGGTTTACCGCAGCTGCCTC[ GCGC ]GTTTCGGTGATGACGGT
          M
          M
          C  G
         MC  G
         MC  G
         AM
          M
         AM
         CM
          M
         CM
                    GAAAACCTCTGACACATGCAGCTCCCGGAGACGGTCACAGC
                                      M

CGG
                                          MCGG
                                           CGG
                                            M
                                           AM
                                           AM
                                            M
                                           CM
                                           CM
```

TABLE III

Cleavage of model substrates by McrBC

| Sub. No. | Pattern of methylation** | Cleavage † of substrate with local sequence of | | | |
|---|---|---|---|---|---|
| | | AluI( § ) | MspI( †† ) | AmC(#)/GmC(*) | CmC(#)/GmC(*) |
| 1 | + + / * * | + | + | NT | NT |
| 2 | * / * * | + | + | NT | NT |
| 3 | * / * | – | – | NT | NT |
| 4 | * / | – | – | NT | NT |
| 5 | * * / * | + | + | NT | NT |
| 6 | * * / | + | + | NT | NT |
| 7 | / * | – | – | NT | NT |

TABLE III-continued

Cleavage of model substrates by McrBC

| Sub. No. | Pattern of methylation** | Cleavage † of substrate with local sequence of ||||
|---|---|---|---|---|---|
| | | AluI(§) | MspI(††) | AmC(#)/GmC(*) | CmC(#)/GmC(*) |
| 8 | ══*══*══ | + | + | NT | NT |
| 9 | ─────── | − | − | NT | NT |
| 10 | ──*──*── | − | − | NT | NT |
| 11 | ══*══*══ over ──*──*── | − | − | NT | NT |
| 12 | ══*══*── | − | − | NT | NT |
| 13 | ──#──#── | NT | NT | + | − |
| 14 | ──#──*── | NT | NT | + | − |
| 15 | ──*──#── | NT | NT | + | − |

**The position of methylation in double-stranded (double line) or single-stranded (single line) oligonucleotide substrates is indicated by the position of * (5'AmC3' or 5'CmC3'). Where the double line is broken, the substrate was first cleaved with HinPI, which cleaves asymmetrically in the oligonucleotide.
† The substrate was (+) or was not (−) cleaved by McrBC. NT, Not Tested.
§ The local sequence around the methylated position was AGmCT.
†† The local sequence around the methylated position was GmCCGG.
The local sequence around the methylated position was not GmC but was either AmC or CmC.

To test local sequence requirements, the oligonucleotide sequence was altered in one of three ways. First, in seven duplexes, the oligonucleotide sequence was altered at five positions, such that MspI (CCGG) sites replaced both AluI (AGCT) sites (Table II (Seq Id NO:8)). The sequence preserved the spacing between methylated bases and placed a G before the methylatable base. Again, methylcytosine was incorporated in the same strand configurations as was done with the duplexes containing AluI sites, and was tested with or without HinPI cleavage. Results for these are shown in the second column of Table III, rows 1-12.

A second alteration in the oligonucleotide sequence tested the permissibility of a C in the position 5' to the methylated base. Three duplexes were synthesised with such changes: one or the other or both of the AGCT sequences contained ACCT instead (Table II (Seq ID NO:8)). For these substrates, one strand was synthesised with m5C at both sites, while the other strand contained no m5C. Results for these are shown in the fourth column of Table III, rows 13-16.

A third alteration in the oligonucleotide sequence tested the permissibility of an A in the position 5' to the methylated base. Three duplexes were synthesised with such changes: one or the other or both of the AGGT sequences contained AACT instead (Table II (Seq ID NO:3)). Again, for these substrates, one strand was synthesised with m5C at both sites, while the other strand contained no m5C. Results for these are shown in the third column of Table III, rows 13-16.

Figure 8A:
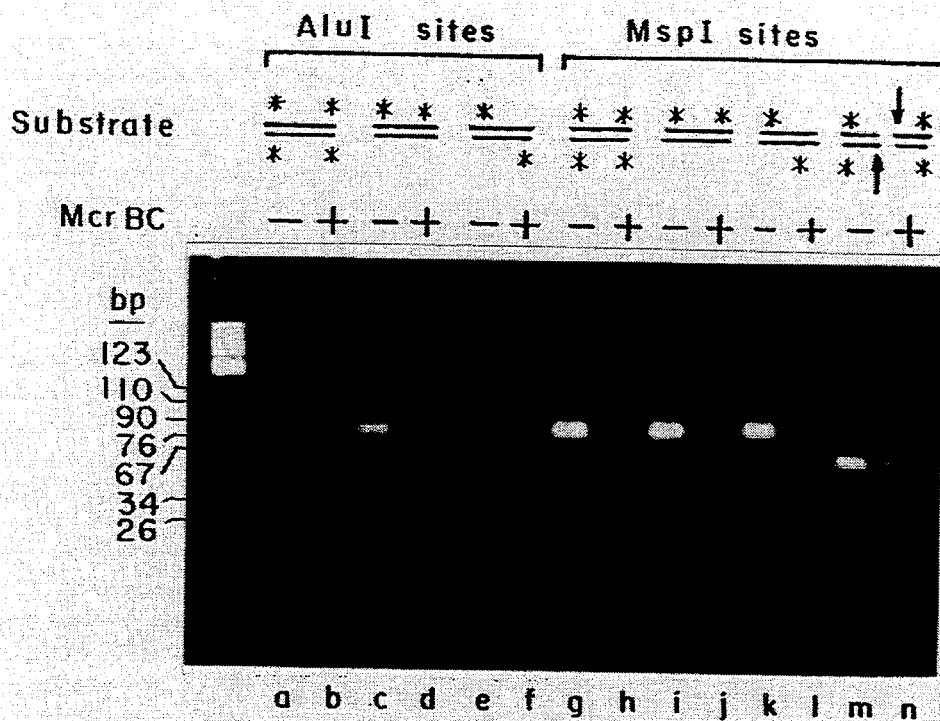
FIG. 8A is a photograph of an agarose gel displaying the products of reactions in which 82 base-pair oligonucleotides were used as substrates.

The oligonucleotide duplexes were made by annealing complementary single strands after boiling in dH2O, mixing in equal molar ratio and cooling to room temperature. Restriction reactions contained 3 µl 10X No-Salt Buffer, 3 µl 10 mM GTP (30 nmol), 0.2 µg (3.7 pmol) oligonucleotide, about 2 µg (40 pmol) McrB$_L$ Fraction III, and about 0.35 µg (8 pmol) McrC fraction Va, in a total volume of 30 µl. The substrate configuration is shown schematically above relevant lanes in FIGS. 8A and B and in Table III. Lanes in FIGS. 8A and B are in pairs, showing unreacted substrate (McrBC not added; −) and the McrBC products after digestion (McrBC added; +). In FIGS. 8A and B, the 82 base-pair oligonucleotide substrates, which contained methylcytosine in either one or in two positions in the sequence on either one or on both strands (indicated by asterisks and hatch marks), were treated with McrBC (+) or not treated (−). In lanes (m) and (n) of FIG. 8A the oligonucleotides were cleaved first with HinPI, which releases a small fragment carrying one methylated position and a large fragment carrying the other. A residual amount of substrate that was not cleaved by HinDPI (lane m) was cleaved by McrBC (lane n).

Cleavage results obtained are shown in Table III above. Results with the duplexes containing AluI sites are given in the column "AluI". Some of the primary data are shown in FIGS. 8A and B. Cleavage required the presence of two methyl groups in the substrate; these could be in trans (in different strands; Table III, line 3 and FIG. 8A, lane g) or in cis (in the same strand; Table III, line 6 and FIG. 8A, lane d). However, they must be appropriately spaced: modification of both strands at the same site ("fully modified" at one AluI site) was not sufficient (Table III, lines 11 and 12). By the same token, it was not necessary that the substrate be "fully modified", but it did not interfere: an oligonucleotide modified in both strands at either or both sites was cleaved as long at the other site had at least one methyl group (Table III, lines 1, 2 and 5; FIG. 8A, lane b), but so was the hemimethylated substrate. Oligomers which were resistant to McrBC include substrates unmethylated (line 9), methylated on one strand at one site (lines 4 and 7), methylated on both strands at one site (line 11), and single stranded DNA regardless of its methylated base content (line 10).

For each sensitive configuration of methyl groups in the substrate set with AluI sites, the corresponding substrate containing MspI sites was also sensitive (Table III, MspI column), and was in fact more efficiently cleaved than the AluI substrate (compare FIG. 8A, lanes h and b; j and d; l and f). This suggests that there are additional sequence-dependent influences on efficiency of cleavage.

Figure 8B:
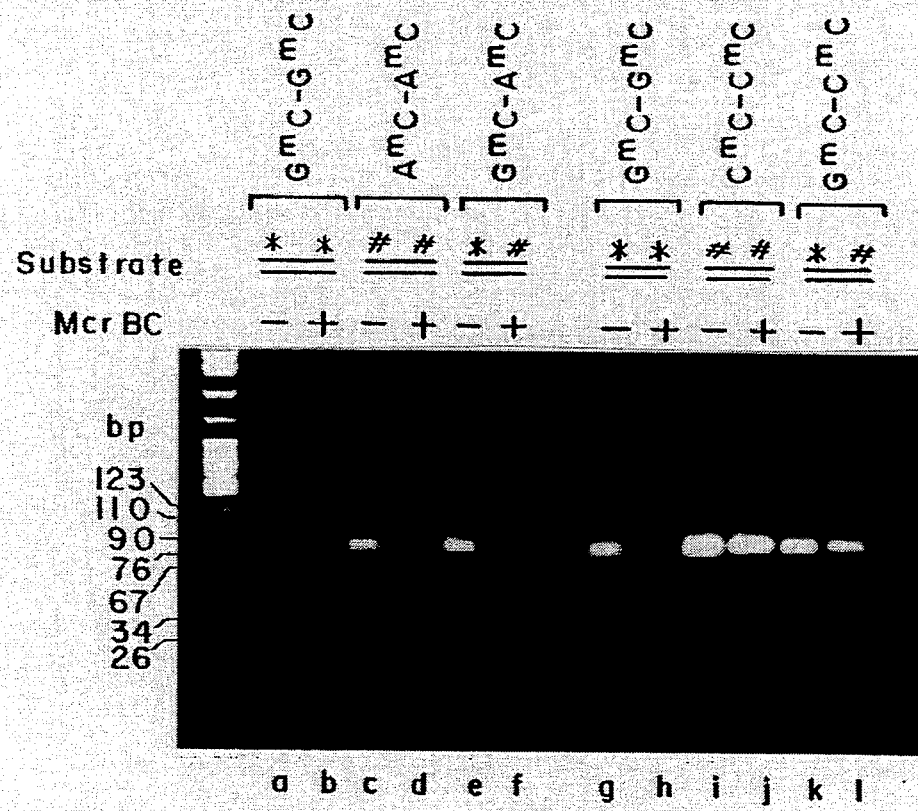
FIG. 8B is a photograph of an agarose gel displaying the products of reactions in which 82 base-pair oligonucleotides were used as substrates.

None of the C substrates was sensitive to cleavage (Table III, lines 13–15; FIG. 8B, lanes j and l), but all of these A substrates were (Table III, lines 13–15; FIG. 8B, lanes d and f).

EXAMPLE V

Dependence of cleavage on GTP; effect of GTP analogues

McrBC activity depends on the presence of GTP. This was revealed in titration experiments similar to those described in EXAMPLE II, except that titration was of the nucleotide rather than the enzyme. McrB$_L$ Fraction IV and McrC Fraction Va (EXAMPLE I), were used, such that each reaction in each series contained 8 pmol McrB$_L$, 8 pmol of McrC (combined activity on the same day of 5 units) and 0.07 pmol of pBR322.AluI in the presence of decreasing concentrations of nucleotides. Mixtures were made up without McrB$_L$ and without nucleotide; nucleotide was added to the first tube in the series; the samples were serially diluted in a manner similar to that described in EXAMPLE I and II; and reactions were begun by addition of McrB$_L$ and transfer to 37° C.

FIG. 2A lanes a–h show the cleavage produced by decreasing concentrations of GTP with a constant amount of enzyme. High levels of GTP (5 mM; lane a) inhibit the enzyme, but cleavage can be detected at 40 nM (lane h). Apparently maximal activity was obtained between 0.62 and 1.25 mM (compare lanes d and e). Accordingly, other nucleotides were tested at 1 mM. Eight guanine nucleotides were tested. Neither GDP or GMP supported cleavage of the substrate, nor did three non-hydrolyzable analogs of GTP tested. The guanosine deoxy-, dideoxy- and ribonucleotide triphosphates all supported the reaction.

The non-hydrolysable analogues inhibited the GTP-supported reaction. They were not equally efficient, however. The addition of GMP-PNP to the assay was at high concentration (5 mM, or 10-fold more than the 0.5 mM GTP in the reaction), and partial inhibition was seen (FIG. 2B). GTP-δ-S was much more effective, with complete inhibition observed with as little as 40 nM of the analogue (FIG. 2B).

ATP also inhibited the reaction, but nonhydrolyzable analogs of ATP did not. Preliminary characterization of the effects of ATP is also shown in FIG. 2A. Lanes i–p show that ATP began to inhibit McrBC activity when equimolar concentrations of ATP and GTP were present (0.5 mM in FIG. 2A; compare lanes l and m with lanes d and e). Full inhibition required five-fold more ATP than GTP in this experiment (2.5 mM; lane j). GTP alone at this concentration supported the reaction normally (lane b). Finally, lanes q–x show that AMP-PNP, a nonhydrolyzable analog of ATP, did not inhibit McrBC. Other experiments (data not shown) have shown partial inhibition of McrBC by high concentrations of AMP-PNP (near 10 mM). Similarly, ATP-gamma-S did not inhibit the enzyme.

EXAMPLE VI

Additional Enzymes That Cleave Methylated DNA

A procedure can be drawn up for detecting enzymes that cleave methylated DNA and obtaining them in pure form. Ten (10) factors facilitate this procedure. These are three requirements and seven additional useful facts or materials. The requirements are:
1. GTP.
2. Modified DNA substrate (e.g. plasmid modified by M.SssI or other site-specific methylase; hmC T4, which is completely substituted with hmC; XP12, which is completely substituted with mC).
3. Knowledge that enzymes of this class are likely to have two subunits corresponding to McrB$_L$ and McrC (hereinafter referred to as "McrB$_L$-type" component and "McrC-type component"), encoded by separate genes corresponding to mcrB and mcrC, which probably need to be purified separately.

The additional useful facts or materials are:
4. Knowledge that one gene corresponding to mcrB probably expresses two proteins, one required for activity; McrB$_L$-type component and one which is believed to inhibit it; McrB$_S$-type component.
5. Knowledge that the enzyme is likely to be active at low pH, a pH at which most extraneous contaminating nucleases are inactive.
6. DNA sequence or probe for each gene.
7. Purified McrB$_L$ and McrC from Escherichia coli K-12, to promote detection of low amounts of activity. These will be designated McrB$_{L,K12}$ and McrC$_{K12}$ in what follows to distinguish them from such proteins from other organisms.
8. Antibody raised against purified McrB$_{L,K12}$ and McrC$_{K12}$, to facilitate identification of the presence of related proteins.
9. Knowledge that a protein structural motif conserved among GTP-binding proteins is likely to be present in McrB$_L$-type component and Mcr$_S$-type component. It was shown that this motif is significant because enzymatic activity requires GTP.
10. Knowledge that the analogue GTP-g-S is likely to inhibit the enzyme at low concentrations and might freeze the enzyme in a DNA-bound state.

Screening for more enzymes like McrBC can be done by the following procedures. As the skilled artisan will appreciate, more than one possible sequence of steps can be tried. The procedure chosen depends on whether a quick result is desired for each organism with a high probability of not finding an enzyme from any; or a slower procedure with a high probability of finding an enzyme in some. For a quick result go directly to Step B1, described below, follow with C(1 and 2) and D also described below; then evaluate the utility of further investigation. For a high probability of finding something, follow the preferred steps identified below. For enteric bacteria use: A2→B(1,2,3)→C(1,2,4,5)→ D→E2→F. For distantly related sources use: A1-→A3→B(1,2,3)→C(1,2,4,5)→D and also →E2-→E1→F.

Step A - Identify likely sources from 1. published reports of instances of biological phenomena like Mcr restriction Acholeplasma (Sladek et al., J. Bacteriol., 165:219–225 (1986)); Bacillus thuringensis (Macaluso & Mettus, J. Bacteriol., 173:1353–1356 (1991)); Streptomyces (MacNail, J. Bacteriol., 170:5607–5612 (1988)).
2. a screen for DNA cross-hybridization at the level of the whole mcrB and/or mcrC genes (Southern blot of enterics gives many positives) requires Factor 6 above.
3. a screen for DNA homology in conserved regions, using PCR and oligonucleotides encoding the conserved protein sequence motif at the GTP-binding site and/or homologous to the conserved intergenic region between HsdS and McrB$_L$-type component requires Factor 9 above.
4. a screen for antibody cross-reactivity in crude extracts requires Factor 7 above.

Step B - Make crude extracts from candidates

1. Native organisms may be used, or, where cloned fragments have been obtained E.coli strains carrying the clones may be used. Cells will be grown in an appropriate medium as described in EXAMPLE I.
2. Make the extracts as described in EXAMPLE I but at low pH (MOPS, ≦6.5), requires Factor 5 above.
3. Examine extracts for antibody cross-reactivity on Western blots and/or ELISA, requires Factor 8 above.

Step C - Test chosen extracts for cleavage

1. Use modified substrates, e.g. those described in Factor 2 above.
2. Reactions should contain GTP at 1 mM; requires Factor 4 above.
3. In standard buffers like those commercially supplied.
4. At low pH; requires Factor 5 above.
5. There are several assays methods as described below.

A major concern is to obtain enough of the relevant proteins to determine whether the sequence specificity is novel. Low levels of expression in the natural situation and the presence of contaminating nucleases may make this difficult. However, there are several novel facts about McrBC$_{K12}$ that will facilitate the task of purifying new proteins sufficiently to determine the nature of the sequence specificity. Seven methods for detecting functional protein to allow purification are described below.

1) Standard cleavage activity-based method.

Cell extracts or fractions are incubated with complex modified DNA substrates in the presence of 1 mM GTP for a suitable time (typically 20 to 60 min) in a suitable buffer, which may be 10 mM MgCl$_2$, 10 mM Tris[C] (pH 7.5), but more preferably a buffer such as MOPS that will buffer at pH 6.5. If cleavage activity is obtained, digest also pBR322.AluI, for which the cleavage pattern obtained with McrBC$_{K12}$ is well known. If a different pattern is obtained, the enzyme has a different recognition site than McrBC$_{K12}$.

2) McrB$_{L,K12}$ complementation cleavage method-detects McrC-type component.

Cell extracts or fractions are incubated as in (1) but with the addition of 2 pmol of purified McrB$_{L,K12}$. This will increase the sensitivity of the method for those novel enzymes that are closely related to the K12 example, sufficient for exchange of subunits.

If cleavage is obtained, test for specificity as in (1). The sequence specificity of the reaction is expected to be determined by the McrC subunit (Dila, et al., J. Bacteriol., 172:4888–4900 (1990)).

4) McrC$_{K12}$ complementation method-detects McrB$_L$-type component.

Cell extracts or fractions are incubated as in (1) but with the addition of 0.4 pmol of purified McrC$_{K12}$. This will increase the sensitivity of the method for those novel enzymes that are closely related to the K12 example, sufficient for exchange of subunits.

If cleavage is obtained, test for specificity as in (1). The sequence specificity of the reaction is expected to be determined by the McrC subunit (Dila, et al., J. Bacteriol., 172:4888–4900 (1990)), so the heterologous combination here is expected to have the K12 specificity. Fractionation and concentration of the novel McrB$_L$ will allow testing of specificity in combination with novel McrC purified by other means.

5) Method based on DNA-binding assays for purification.

This is a gel retardation assay. Binding of the whole enzyme or binding of the subunit responsible for DNA site recognition may result in retention of a methylated oligonucleotide in polyacrylamide gels. The oligonucleotide required is not immediately predictable, but methylation of all C residues in a complex sequence of ~100–200 bp is recommended. Such experiments are done using labeled fragment and unlabelled non-specific competitor to avoid isolation of complexes with irrelevant DNA-binding proteins. Here, non-specific competitor DNA should ideally be unmethylated DNA of the same sequence This method has been used for purification of eukaryotic regulatory proteins. It may not require that the entire enzyme be functional. This could be tried with or without complementation by purified McrB$_{L,K12}$ or McrC$_{L,K12}$ and with and without GTP present (in the presence of EDTA).

This procedure is most likely to obtain an McrC analogue, since McrC is probably the DNA-binding moiety.

Testing of specificity should be done in combination with both McrB$_{L,K12}$ and McrC$_{K12}$, to verify the identity of the binding moiety, as well as, preferably the other novel subunit if missing.

6) Method based on release from inhibition

GTP-g-S was shown to completely inhibit the McrBC$_{K12}$-mediated reaction, presumably because the enzyme binds the nucleotide and will not release it. If GTP-g-S is added at concentrations low enough to allow a small amount of reaction (e.g. less than equimolar with the amount of McrB$_{K12}$ present) then addition of competing McrB$_L$-type component to the reaction should further reduce the amount of GTP-g-S available to inhibit the McrBC$_{K12}$-mediated reaction and increase apparent reactivity. This will allow purification of any protein that allows competition with McrB$_L$-type component for this nucleotide. Caution must be excercised that this is not an extraneous GTP-binding protein. This is likely to yield McrB$_L$-type component or McrB$_S$-type component. Purified or concentrated fractions can be used to reconstitute activity in the presence of the novel McrC-type component obtained by other means.

7) Combination method based on 4 and 5 above.

GTP probably acts in a reaction cycle like those of other GTP-binding proteins: Component 1 can interact with component 2 only when GTP is bound; component 1+2 can interact with component 3 only when GDP is bound, and this can happen only when bound GTP is hydrolysed; the complex of 1+2+3 must disassociate in order to recycle and this can happen only when GDP has been released. GTP-g-S probably acts by preventing the hydrolysis step, and thus the reaction is frozen at 1+2. If the three components are DNA, McrB$_L$-type component and McrC-type component, then GTP-g-S may freeze the reaction in a DNA-bound state, which would increase the sensitivity of a gel-retardation step as in B by preventing dissociation of the bound complex. Alternatively, use of labeled GTP-g-S may allow purification by addition of radioactively-labelled nucleotide to the extract and chromatography using the label as an assay. This method is most likely to yield a mixture of both subunits.

Step D - Cloning for increased production and ease of detection

If DNA cross-hybridization or PCR was used in selecting examples, try to clone large fragments (>3 kb) carrying the hybridizing segment or the segment isolated by PCR using standard hybridization and cloning methods. Expression at levels detectable in vitro may be expected if the organism is reasonably close to E.coli (e.g. Enterobacteriacea). This may also be true if the organism of origin is Bacillus. It is less likely if the organism is Streptomyces or other G+C-rich organism.

Step E - Partial purification of enzyme for identification of site recognized

For those cases where detection was successful using the complementation methods (C5ii, iii), efforts should concentrate on purification of McrC-type component (part 2 below), because this is likely the subunit that confers sequence specificity (Dila, et al., 1990). Mapping experiments (Step F) using pure McrB$_{L,K12}$ and partially purified McrC-type component of novel origin will quickly determine whether the specificity is novel and worth further pursuit. For more distantly related enzymes, both subunits must be purified. Purification of the McrB$_L$ is likely to be more difficult due to the probable presence of the inhibitory McrB$_S$.

1. McrB$_L$-type component
   a. Chromatograph over DEAE Sepharose, eluting with a 0.05–0.5M linear NaCl gradient; expect McrB$_L$-type component activity at ~0.25M.
   b. Identify the relevant fractions by methods described in A4 or C5 and characterized at Step C:
      i. test them for DNA cleavage in the presence of purified McrC$_{K12}$. Use 0.2 mg substrate, 0.4 pmol of McrC-type component, 1 mM GTP in a volume of 20 ml for 20 min at 37° C. The number of assays required is N for N fractions, and the amount of McrC-type component present is reasonably certain to be sufficient to allow detection of small amounts of McrB$_L$-type component activity;
      ii. alternatively, test fractions for crossreactivity on Western blot or by ELISA. For example, run 10 ml (up to 10 mg) of fraction on a polyacrylamide gel; transfer protein bands to Immobilon by a standard electroblotting procedure; react with anti-McrB$_{L,K12}$, for example from mouse; and visualize by standard antibody-conjugated alkaline phosphatase and chromogenic substrate by standard procedures. Number of assays required is N for N fractions; this requires Factor 8 above;
      iii. alternatively, test fractions for DNA cleavage against each other in all combinations. Conditions as in (i) above except that 8 1 of each fraction should be used. The number of assays required is $N^2$ and it is quite possible that there will not be enough McrB$_L$-type component or McrC-type component to allow detection of activity. This procedure may be required for distantly related enzymes;
   c. Pool the positive fractions. If pool is sufficiently concentrated and free of contaminating nucleases, then go on to Step F.
   d. Follow with chromatography on Heparin Sepharose, eluting with a 0.1–1M linear gradient of NaCl; expect McrB$_L$-type component activity at ~0.25M
   e. Identify relevant fractions as determined in 1b
   f. Pool positive fractions as in (c)
   g. Repeat with other standard resins (phosphocellulose, hydroxylapatite, Affi-gel Blue) until Step F is practical.
2. McrC
   a. Chromatograph over Phosphocellulose, eluting with a 0.2–1M linear NaCl gradient; expect McrC-type component activity at ~0.5M.
   b. Identify the relevant fractions by methods described by A4 or C5 and determined at Step C.
   c. Pool the positive fractions. If sufficiently concentrated and free of nucleases go on to Step F.
   d. Follow with chromatography on Hydroxylapattte, eluting with a 0.01–0.7M linear gradient of KPO$_4$; expect McrC-type component activity at ~0.2M
   e. Identify relevant fractions as in (b)
   f. Pool positive fractions. If sufficiently concentrated and free of nucleases go on to Step F.
   g. Repeat with other standard resins.

Step F - Distinguishing enzyme from McrBC$_{K12}$

Digest pBR322.AluI, pBR322.HhaI, pUC19.MspI and pUC19.HaeIII with fractions purified in VA, VB. Distinguish pattern from that of McrBC$_{K12}$ on the same substrates. For those cases where in vitro complementation is possible, use McrB$_{L,K12}$ together with the novel McrC in this experiment.

Step G - Preparing for overproduction

1. Use clones obtained at Step A and D, or use methods described in Steps A and D to obtain clones.
2. Complete sequence; if necessary obtain adjacent clones to obtain complete gene(s).
3. Identify possible start codons.
4. Construct PCR primers similar to those used in creation of K12 constructs. It may be necessary to test more than one possible start site. For McrG-type component, the aim is to fuse the N-terminal amino acid to the vector ribosome-binding site and ATG. For McrB$_L$-type component, the goal is to do the same and simultaneously to suppress translation initiation at internal sites resulting in production of McrB$_S$, which is inhibitory. (A regulatory function of this kind is likely to be conserved in many cases but the same regulatory result might be obtained by other means in some examples. Necessity for worrying about this can be assessed by Western blot of natural isolates and preliminary overproducers described above). These goals can be met by careful comparison of the sequence obtained from the new system with that of the K12 system and choice of starts at positions similar to those used for production of the K12 enzyme.

5. Clone PCR products into pAII17.
6. Test for overproduction of McrB$_L$-type component and McrC-type component by polyacrylamide gel electrophoresis; antibody may be used to verify identity and number of the protein products. If McrB$_S$-type component is made by the overproducer, try a different start or a different translation vector.

Step H - Overproduction

Grow cells, induce, and purify according to the procedure in EXAMPLE I above.

EXAMPLE VII

Detection of Developmental Abnormalities Mediated by Imprinting or Other Changes in DNA Modification State Prader-Willi and Angelman's syndromes are mental retardation disorders with different clinical manifestations. Cytologically apparent deletions of chromosome 15 are found in many such patients. The deletions found in the two syndromes are not distinguishable from each other. This suggests that the gone(s) involved are physically very closely linked, and also suggests that loss of expression of (a) deleted gone(s) is causally related to these diseases. However, some patients with each syndrome have no deletion that can be detected cytologically or with molecular probes to the chromosomal segment involved (15q11q13) (Knoll et al., Am. J. Hum. Genet., 48:16-21 (1991); Malcolm et al., Lancet., 337:694-697 (1991); Zori et al., Am. J. Med. Genet., 37:294-295 (1990)).

Prader-Willi and Angelman syndromes show inheritance patterns characteristic of imprinting, differing in whether the deletion alleles are inherited through the mother or through the father (Knoll, et al., Am. J. Hum. Genet., 48:16-21 (1991); Malcolm, et al., Lancet., 337:694-697 (1991); Zori, et al., Am. J. Med. Genet., 37:294-295 (1990)). Recent development of molecular probes for the region involved (Cantu et al., Am. J. Hum. Genet., Abstr. 49 (suppl.):281 (1991); Driscoll et al., Am. J. Hum. Genet., Abstr. 49 (suppl.) 394 (1991); Nicholls et al., Am. J. Hum. Genet., Abstr. 49 (suppl.):334 (1991)), have allowed workers to show that DNA methylation patterns also show patterns expected if imprinting is caused by or faithfully reflected by methyation state (Driscoll, et al., Am. J. Hum. Genet., Abstr. 49 (suppl.) 394 (1991)). One of these molecular probes is DN34. Detection of methylation state in this instance was done by the MspI/HpaII Southern blotting method.

McrBC is a modification-specific, sequence-specific restriction endonuclease. The site recognized, R$^m$C(N$_{40-80}$)R$^m$C, overlaps the modification site of the mammalian methylase: R$^m$CG(Nx)R$^m$CG. Approximately one-half of modified sites should be present in the context R$^m$C. Where the density of modification is high (as is true near inactivated genes), most of these should be within appropriate distance of another such site, and cleavage will occur between the two sites. Where the density of modification is low (as is true near actively expressed genes), cleavage will not occur. Thus, digestion products from a gene that is inactive should be smaller than products from a gene that is active.

A. A Diagnostic Kit may be Designed with the Following Constituents

McrBC: for cleaving DNA containing the recognition sequence R$^m$C(N$_{40-80}$)R$^m$C.
10X Buffer: 100 mM Tris (pH 7.5), 100 mM MgCl$_2$; or 100 mM MOPS pH 6.5, 100 mM MgCl$_2$.
GTP: 10 mM, pH 7.0
Stop dye: 50% glycerol, 1% SDS, 0.25% bromophenol blue, 0.25% xylene cyanol
A labelled DNA containing the sequence of DN34.
A labelled DNA containing a positive control sequence that detects a sequence for which methylation state does not vary, for example, c-Ha-ras-1 (Silva & White, Cell, 54:145-152 (1988)).

B. Procedure for Obtaining DNAs

DNA samples for analysis may be isolated by standard methods (Strauss, 1990) from patient tissues; for example from $-3 \times 10^6$ peripheral blood leukocytes ($\sim$15 ml blood). At least one set of samples should be from a normal control.

Labelled DNA probes may be plasmids labeled by nick translation (Rigby et al., J. Mol. Biol., 113:237-251 (1977)) or random priming (Tabor et al., Current Protocols in Molecular Biology, (Ausubel, F.M., et al.), pp. 3.5.1-3.5.15, John Wiley & Sons, New York (1990)) with detection by radiolabel or non-radioactive methods. They may also be synthetic oligonucleotides homologous to the sequence of interest labelled with radiolabel or non-radioactive methods (Ellington & Green, Current Protocols in Molecular Biology, (Ausubel, F.M., et al.), pp. 2.11.1-2.11.18, John Wiley & Sons, New York (1990)).

C. DNA digestion

For each source of test DNA and also for the control DNA sample, make up three tubes as follows:
10 ml 10X buffer
10 ml GTP
DNA (5 mg)
dH$_2$O to a final volume of 100 ml
Add 50, 100 or 150 units of McrBC to each of the three tubes in each set
Incubate for 4 hours at 37° C.
Stop with 10 ml stop dye D. Analysis Divide each sample and run on two 1% TBE-agarose gels (400 mA-h for a 150 mm gel; (Voytas, Current Protocols in Molecular Biology (Ausubel, F.M., et al.), pp. Unit 2.5A, Green Publishing Associates, New York (1990)). Transfer to filters by Southern or electroblotting procedures, probe the membranes and visualize by autoradiography or other suitable detection method (Selden et al., Current Protocols in Molecular Biology (Ausubel, F.M., et al.), pp. Unit 2.9, Green Publishing Associates, New York (1990)). One filter should be probed with the DN30 and the other with the control. The control probe should detect an identical band in all cases and will reveal partial digestion or improper transfer, while the control sample DNA will reveal the position of the expressed normal gene. Absence of a signal in this position for the test sample will indicate the presence of one of the following: deletion of both copies of the gene; deletion of one copy and methylation of the other copy; or methylation of both copies.

E. Improvements

1. Further investigation should enable simplification of this procedure by enabling specification of a control probe that is suitable for use on the same filter as the test probe (i.e. the expected control fragment will not interfere with interpretation of the fragments detected by the test probe). Control and test probing of the same filter improve the reliability of the control for DNA transfer.
2. Suitable double digestions may also simplify incorporation of the control into the same filter.
3. Depending on the sizes of fragments generated, a polyacrylamide gel or a higher percentage agarose gel may give clearer results for this procedure.
4. Design of suitable PCR primers might allow the use of much smaller amounts of test DNA (of the order of 100 l of blood). In this case, PCR primers would be designed to flank the location of of cleavage; in the absence of cleavage, a product would be produced, while in the presence of cleavage, no product would be produced. The products before and after McrBC treatment of the starting DNA would be compared. This would enable distinction to be drawn between patients homozygous for deletions (where no product will be produced in either sample) and patients with homozygous or hemizygous for modification at the relevant site (where product will be produced before but not after cleavage). It would also provide material for use in sequence-based detection methods, where the expressed copy contains a point mutation rather than a deletion. The procedure should be generalizable to detection of abnormal methylation patterns that might result in certain cancerous transformation events, developmental abnormalities (some birth defects, for example), or other similar genetic diseases.

EXAMPLE VIII

Construction of pER273 and pER276

A. The vector

The vector, pAII17, was constructed by inserting a ~750 bp BamHI-SphI fragment with a fourfold repeat of the rrnB transcription terminator upstream of the T7 promoter in the vector pET11c (Studier et al., 1990). The fragment was obtained by digesting pRS415, (Simons, 1987), with EcoO109I, repairing the ends with Klenow fragment, adding SphI linkers (New England BioLabs #1047) and digesting with SphI and BamHI. The vector PET11c was prepared by digestion with EcoRI and HindIII, repair with Klenow fragment, and recircularization with T4 DNA ligase, to create pAIF. pAIF was then digested with SphI and BglII and ligated with the BamHI-SphI fragment to create pAII17.

B. pER273 and pER276

McrB$_L$ and McrC overproducer plasmids were created using the polymerase chain reaction (PCR) to create a fragment allowing a precise fusion of the mcrB and mcrC reading frames to the translation signals of pAII17. The primers used for the mcrB construction were #1: 5' GAGGAAGGCATATCATATG-GAATC 3' (Seq ID NO:9); and #2: 5'CGGGATC-CGACAGGTATCACGGGC 3'(Seq ID NO:10). Primer #1 is identical with the sequence between bp 3 and 25 of the sequence in (Dila, et al., 1990) except for one mismatch at bp 15. It creates an NdeI site with which to fuse the second ATG of the mcrB frame (position 18) to the vector translation signals. The primers used for the mcrC construction were #3: 5'CCCCTATAAACAACACATATGGACCAAC 3' (Seq ID NO:11); and #4: 5'CGGGATCC-CTATAAAACTTACCGC 3' (Seq ID NO:12). Prime #3 ' is identical with the sequence between 1349 and 1376 except for two mismatches at 1364 and 1366, creating an NdeI site with which to fuse the first ATG of the mcrC frame (position 1367). Primers #2 and #4 are complementary to sequence from 1407–1411 and from 2443–2459, with an 8-base 5' extension containing a BamHI site. The DNA substrate for PCR was pDD87, a plasmid essentially identical to pDD90 (Dila, et al., 1990), carrying the ~2700 bp mcrBC fragment at the BamHI site of the pACYC184-derived pDD34 vector (Dila, et al., 1990).

The polymerase chain reaction was carried out using Vent TM DNA polymerase in the Vent TM buffer with 0.2 mM each primer, 4 mM MgSO$_4$, 100 mg/ml BSA, and 200 mM each dNTP in a reaction volume of 50 ml with 10 ng of pDD87 DNA substrate. All components except the polymerase were mixed, the mixture was placed at 72° C. in a Techne PHC-2 thermal cycler, Vent TM polymerase was added (1 units), the mixture was overlaid with 50 ml light mineral oil (Fisher) and the chain reaction was begun. Denaturation was at 95° C. for 1 min, annealing was at 60° C. for 1 min and extension was at 72° C. for 1.5 min, with a ramp speed of 4 between segments. 20 cycles were carried out, with an extra 45 seconds at 72° C. added to the final extension reaction. Products were transferred to new tubes, extracted with an equal volume of phenol/ClCl$_3$ (50:50 v/v), precipitated in the presence of 1 mg tRNA with 2M NH$_4$SO$_4$ and 1 volume isopropanol, washed with 100 ml 70% EtOH and resuspended in DNA buffer (10 mM Tris pH 7.5, 1 mM EDTA).

PCR products as well as the vector were digested separately with BamHI and NdeI, phenol extracted, precipitated twice with isopropanol, and approximately 20 ng each of insert and vector were ligated in a 20 ml reaction volume. Ligation products were introduced into ER1821 by transformation. Transformants carrying the appropriate mcrB and mcrC constructs were designated pER273 and pER276, respectively (FIGS. 3 and 5).

EXAMPLE IX

Inhibition of McrBC Restriction Activity Using McrB$_S$

McrB$_S$ was expressed from a low-copy construct (pDD99), with expression presumably directed by native transcription and translation signals. The McrB$_L$ protein was not expressed due to a translational frameshift caused by filling in a BspMI site early in the mcrB gene. The four-base insertion resulted in translation termination eight codons downstream of the filled in site to yield a presumptive 49 amino-acid product (6.1 kDa predicted MW). The McrC product was not expressed due to an in-frame deletion of 627 bp within the mcrC gene. The truncated McrC product would have a predicted MW of 14.7 kDa.

Strains containing a chromosomal copy of the wild type operon, or a deletion of the entire operon, were tested for restriction activity directed against infecting λ phage modified by M.HaeII, in the presence or the absence of this plasmid. The wild-type strain without the McrB$_S$ plasmid restricts this phage, reducing plaque formation by 33-fold compared with the number formed on the deletion strain without the plasmid. In contrast, when the wild-type strain contained the McrB$_S$ plasmid, it failed to restrict: the same number of plaques were formed as were formed on deletion strain. Plaques formed on the deletion strain were the same with or without the McrB$_S$ plasmid. Therefore, even modest extra expression of McrB$_S$, such as that expected from the low-copy construct, inhibits the restriction activity expressed by a chromosomal wild-type copy of the mcrBC genes in vivo.

pDD99 was made from pDD87. This starting plasmid carrying the entire mcrBC operon was derived from pACYC184, via pDD34. pDD34 has a cassette of the intergenic region of phage f1 inserted at the ClaI site (Dila et al., J. Bacteriol., 172:4888–4900 (1990)), and pDD87 has a 2.7 kb HpaI-StUI fragment carrying mcrBC with BamHI linkers added inserted at the BamHI site of pACYC184. It is substantially identical to pDD90, which was described in (Dila, et al., J. Bacteriol., 172:4888–4900 (1990)).

Cesium chloride-purified DNA was cleaved treated with BspMI (lot 11; 4 units). Reaction contained 2 mg DNA in 1X BssHI buffer (NEB) in 50 µ21 and was incubated at 37° C. At intervals (30 min, 1 h, and 1.5 h), 16 µl was withdrawn and transferred to a new tube (the same tube for all three points) containing 2 µl of 0.5M EDTA to stop reaction. The combined partial digests were precipitated overnight by addition of 20 µl 5M NH$_4$ Acetate and 100 ml isopropanol and incubation overnight at 4° C. The DNA was then resuspended in 1X fill-in buffer with 100 mM each dNTP, 1 µl Klenow fragment was added (New England BioLabs lot #47, 5 units), incubated at 37° C. for 30 min and run on a minigel of low-melting point agarose (FMC Bioproducts). Bands were visualized with longwave ultraviolet light, the linear band excised and the gel (about 100 µl) melted at 65° C. for 10 min in an eppendorf tube. Ligation was carried out by adding, to 20 µl of gel 25 µl 2X blunt-ligation buffer, 5 µl 10 mM ATP and 1 µl (2000 units) of concentrated ligase. This was incubated for 3 hours at 14° C.

100 µl of frozen competent ER1648 cells were transformed (Maniatis et al., 1982) with 20 ml of the ligation mixture. After outgrowth of the mixture in 1 ml of Rich Broth in a plating tube in the gyrotory water-bath shaker at 37° C., 0.3 ml was plated on Rich plates with chloramphenicol (15 µg/ml).

49 of the transformants obtained were tested for restriction of T4gt by cross-streaking from colonies with a toothpick across a line of phage suspension laid down on a Phage plate as described in (Dila, et al., J. Bacteriol., 172:4888–4900 (1990)). Two transformants failed to restrict the phage. Plasmid DNA was made from these two and from two others by the boiling prep method (Maniatis, et al., 1982), digested separately with BspMI and SalI, and the two digests and an uncut sample for each were run on an agarose gel. One of the non-restricting plasmids had the expected digest patterns and was designated pDD98.

Minicleared lysates (7.6 ng/ml) were then made from this. 10 µl of this was digested with NsiI (5 units) in 1X NEBuffer 2 in a final volume of 50 µl for 1 hour at 37° C. The digest was heated (60° C. 10 min) and precipitated (20 µl NH$_4$ Acetate, 100 µl isopropanol overnight at 4$\rho$C) resuspended in 1X ligase buffer with 1 mMATP and 1 µl concentrated ligase, incubated at 14$\rho$C for 3 h, and heated to kill the enzymes. 100 µl of frozen competent ER1648 was transformed with 20 µl of ligation mixture and plated on Rich plates with chloramphenicol as above. Four of twenty transformants examined had the correct structure when examined by digests with NsiI and one was designated pDD99 (also called "fill-in del NSiI" or FIDN). A similar deletion construction from pDD87 at the same time was designated pDD100 (also called "del NsiI" or "DN").

In vitro transcription-translation reactions were carried out using the DuPont-NEN DNA expression system (prokaryotic) (Cat # NEK-038 system lot #0646WKO), L-[$^{35}$S] methionine and cesium chloride purified DNA of pDD87 (WT), pDD98 (FI), pDD99 (FIDN) and pDD100 (DN) and pDD34 (vector). All materials were thawed and kept on ice before use except that [$^{32}$S]-methtonine was kept at room temperature. Reactions contained one µg DNA (1 µl), 3 µl S-30 extract from the kit, and 6 ml of a premix consisting of 6 ml dH$_2$O, 36 µl cocktail B from the kit, and 30 µl [$^{35}$S]-methionine (10.41 mCi/ml, 1186 Ci/mmol). Tubes were vortexed, pulse-spun and incubated for 45 min at 37° C. They were then pulse-spun again, 1 µl RNAse A (10 mg/ml) was added and reactions were incubated a further 15 min at 37$\rho$C. 5.5 µl running dye was added, samples were boiled for three minutes and the mixture spun for five minutes. Samples were diluted fifteen fold in 1X running buffer and 16 µl were loaded onto a precast 12-20% gradient polyacrylamide gel (ISS-Enprotech) with molecular weight markers. The gel was run for 4 hours at 80 V and fixed overnight in acetic acid/methanol (40 ml dH$_2$O, 10 ml glacial acetic acid and 50 ml methanol) on a rotator at room temperature covered with parafilm. The gel was air dried between sheets of plastic film and autoradiographed (18 hours).

Figure 9:
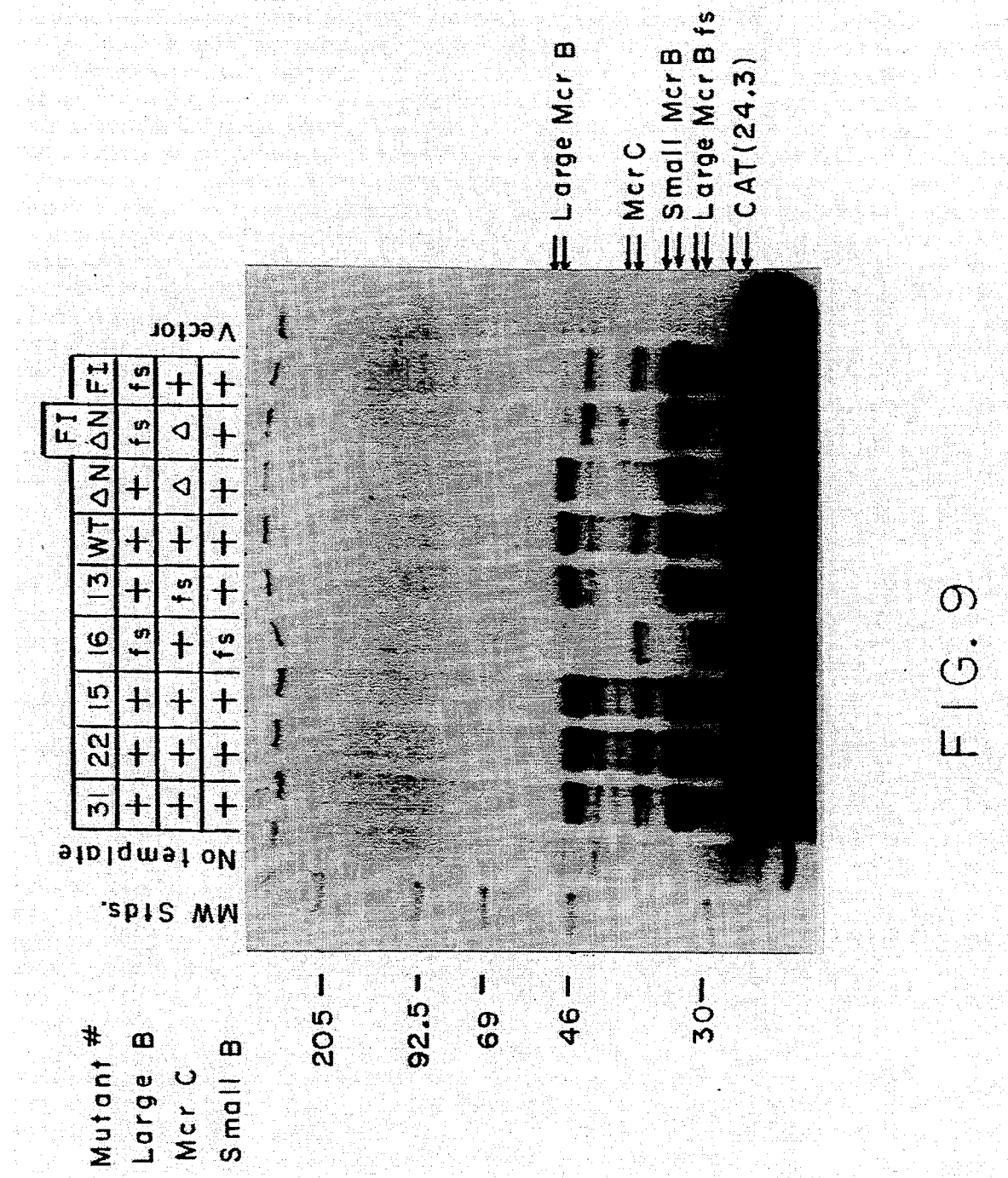
FIG. 9 is photograph of a polyacrylamide gel displaying proteins made by mutant McrBC plasmids.

Results are shown in FIG. 9, right-hand five lanes. Each of the bands seen runs as a doublet, probably because the samples were not boiled long enough. The positions of chloramphenicol transacetylase (CAT), Large McrB$_L$, Small McrB$_L$ and McrC are indicated with arrows, as is the position of a frameshift product from another plasmid run on the same gel (Large McrB$_L$ fs).

It can be seen that pDD87 (WT) directs synthesis of four doublets corresponding to McrB$_L$, McrC, McrB$_S$ and CAT; pDD100 (DN) directs synthesis of three doublets corresponding to McrB$_L$, McrB$_S$ and CAT; pDD99 (FIDN) directs synthesis of McrB$_S$ and CAT; and pDD98 (FI) directs synthesis of McrC, McrB$_S$, and CAT. This confirms that the fill-in mutation abolished synthesis of McrB$_L$ without affecting synthesis of McrB$_S$, that the NsiI deletion abolished synthesis of McrC without affecting synthesis of either McrB$_L$ product, and that the double mutant expressed only McrB$_S$ in addition to the vector product, CAT.

Restriction tests made use of two strains: the wild-type (ER1564: F$^-$ fhuA2 Δ(lacZ)r1 supE44 trp-31 mcrA1272::Tn10 his-1 argG6 rpsL104 xyl-7 metB1 hsdR2) and the mcrBC deletion (ER1648: F$^-$ fhuA2 Δ(lacZ)r1 supE44 trp-31 mcrA1272::Tn10 his-1 rpsL104 xyl-7 metB1 Δ(mcrCB-hsdSMR-mrr)102::Tn10). The vector alone (pDD34), McrB$_S$ plasmid (pDD99), the McrB$_L$+McrB$_S$ plasmid (pDD100), the McrB$_S$+McrC plasmid (pDD98) and the wild-type plasmid (pDD87) were introduced into these strains by CaCl$_2$ transformation with selection for chloramplenicol resistance (Maniatis, et al., Molecular Cloning: a laboratory manual, Cold Spring Harbor Laboratory, Cold Spring Harbor, New York (1982)). Colonies were picked, streaked to repurify, and 1 ml overnight cultures grown in Rich Broth with chloramphenicol.

The phage used to test restriction was λ modified by M.HaeII (λ.HaeII). ER1565 (F− fhuA2 Δ(lacZ)r1 supE44 trp-31 mcrA1272::Tn10 his-1 argG6 rpsL104 xyl-7 metB1 mcrB1 hsdR2) transformed with pER82 (MHaeII+, Ap+) was used as the host for growing the modified stock. A colony of ER1565/pER82 was grown in 10 ml Rich Amp (per liter 10 g Bacto-Tryptone (Difco), 5 g NaCl (Sigma), 5 g Yeast Extract (Difco), 100 μg/ml ampicillin (Sigma)) overnight; the next day culture was subcultured 0.1 ml/2 ml λYMAmp (per liter 10 g Bacto-Tryptone (Difco), 2.5 g NaCl (Sigma), 2 g maltose (Sigma), 100 μg/ml ampicillin (Sigma)) over the day (~8 h); in the evening a stock of phage was streaked on a λ plate (per liter 10 g tryprone, 2.5 g NaCl, 10 g Bacto Agar) and overlaid with 2 ml of a suspension of the overday in top agar (0.1 ml culture/2ml Top agar; Top agar, per liter 10 g Tryprone, 5 g. NaCl, 0.5 g $MgCl_2.6H_2O$, 6 g. agar).

The plate was incubated at 37° C. overnight, and the bacterial culture was stored at 4° C. Fresh plates were poured the next morning. The bacterial culture was diluted 0.1 ml/5 ml 1YMAmp and grown to a density of 49 Klett units. Two plaques from the streak plate were picked with a sterile capillary pipet into 3 ml of the subculture of ER1565/pER82, vortexed, incubated at room temperature for 10 minutes diluted with 7.5 ml Top agar and plated on three λ plates. Plates were incubated at 37° C. for four hours until clear, scraped with a sterile glass spreader into a 50 ml Oak Ridge centrifuge tube with a few drops of chloroform, the plates were rinsed with 1 ml each λdil (10 mM Tris, pH 7.5, 10 mM $MgSO_4$), and the combined mixture was centrifuged at 8,000 rpm in a Beckman high-speed centrifuge. The supernatant was poured off into a 6 ml screwcap tube with chloroform.

The restriction test was done as follows. Cultures described above were subcultured (50 ml into 2 ml λ+Chloramphenicol 15 μg/ml), grown on a rollordrum (New Brunswick Scientific) to a density of 60 Klett units. 0.2 ml of each culture was plated in 2.5 ml Top agar on a λ plate. The phage suspension was diluted in λdil by a factor of $10^{-4}$, $10^{-5}$, and $10^{-6}$ and 30 μl spots of each suspension were placed on the surface of each plate. After air drying, the plates were incubated overnight at 37° C. and plaques were counted. The results are shown in Table V below. Inactivation of $McrB_L$ or McrC individually is sufficient to prevent the plasmid from mediating restriction in a deletion host (compare lines 3 and 4 with line 2, fifth and sixth columns). Further, any construct that makes $McrB_S$ in an unbalanced ratio to the other two products reduced the efficiency of restriction by wild type, which is already competent to restrict (compare lines 1 and 2 with 3-5, third and fourth columns). $McrB_S$ alone is sufficient to effect this result, and has the strongest effect of the three plasmids (line 5). It is concluded that $McrB_S$ inhibits the action of $McrB_L$+McrC.

TABLE V

| Plasmid | Plasmid-determined Mcr products | Wild Type (ER1564)* A* | Plating efficiency (Ax/B1) | Deletion (ER1565) B* | Plating efficiency Bx/B1 |
|---|---|---|---|---|---|
| 1. pDD34 | none | 1 | 0.04 | 28 | (1) |
| 2. pDD87 | $B_L$, $B_S$, C | <1 | <0.04 | 2.1 | 0.08 |
| 3. pDD100 | $B_L$, $B_S$ | 13.1 | 0.46 | 40 | 1.4 |
| 4. pDD98 | $B_S$, C | 5.2 | 0.18 | 31 | 1.1 |
| 5. pDD99 | $B_S$ | 18 | 0.64 | 35 | 1.25 |

*The numbers represent the weighted average number of plaques, normalized to the result that would be observed at the $10^{-5}$ dilution. For example, for ER1564/pDD100, 125 plaques were obtained on $10^{-4}$ dilution; the expectation for $10^{-5}$ dilution based on this would be 12.5 (0.1 × $10^{-4}$ value). 20 were observed, but statistically this is close to expectation because of sampling error. A weighted average of the two numbers, accounting for the different dilutions would, be (125 + 20) ÷ 1.1 = 132; but this is an average for the $10^{-4}$ dilution; the number for $10^{-5}$ dilution would be 13.2, which is the number entered in the Table.

---

What is claimed is:

1. A recombinant modified cytosine restriction endonuclease, McrBC, obtainable from Escherichia coli comprising two active components McrB$_L$ and McrC, wherein the endonuclease cleaves a methylated DNA fragment at the Rm5C (N40–100) Rm5C recognition site.

2. The recombinant endonuclease, McrBC, of claim 1, wherein said endonuclease is substantially free of McrB$_S$.

3. A construct comprising a nucleic acid sequence encoding the McrB$_L$ component of the McrBC endonuclease, wherein said construct substantially does not express McrB$_S$.

4. A construct which is pER276.

5. A recombinant vector which comprises the construct of claim 3.

6. A recombinant vector which comprises the construct of claim 4.

7. A host containing the recombinant vector of claim 5.

8. A host containing the recombinant vector of claim 6.

9. A construct comprising a nucleic acid sequence encoding the McrB$_L$ and McrC component of the McrBC endonuclease, wherein said construct substantially does not express McrB$_S$.

10. A recombinant vector which comprises the construct of claim 9.

11. A host comprising the recombinant vector of claim 10.

12. The construct of claim 3, wherein said construct is pER273.

13. A method for producing recombinant McrBC having two active components McrB$_L$ and McrC, comprising isolating a nucleic acid sequence encoding McrB$_L$ and nucleic acid sequence encoding McrC, inserting the isolated DNA into the same or separate vectors to form one or more recombinant vectors, transforming a host cell with the one or more recombinant vectors and culturing the transformed host cells under conditions suitable for expression of the active components of the McrBC nuclease.

14. The method of claim 13 wherein the isolated DNA is inserted into the same vector.

15. The method of claim 13 wherein the isolated DNA is inserted into separate vectors.

16. A method of treating cytosine-modified DNA with recombinant endonuclease, McrBC, which has two active components McrB$_L$ and McrC, comprising determining a recognition sequence of the McrBC endonuclease for a cytosine-modified DNA, mapping locations for McrBC cleavage, and digesting the cytosine-modified DNA substrate with McrBC endonuclease.

17. A method of cleaving cytosine-modified DNA having the sequence Rm5C (N40–100) 5m5c with recombinant endonuclease McrBC which has two active components, McrB$_L$ and McrC, comprising contacting the cytosine-modified DNA with the McrBC endonuclease under suitable conditions.

* * * * *

UNITED STATES PATENT AND TRADEMARK OFFICE
CERTIFICATE OF CORRECTION

PATENT NO. : 5,405,760

DATED : April 11, 1995

INVENTOR(S) : Raleigh, et al.

Page 1 of 15

It is certified that error appears in the above-indentified patent and that said Letters Patent is hereby corrected as shown below:

Column 1, line 34, replace "Bickle, I.A." with --Bickle, T.A.--

Column 1, line 59, replace "(1988))." with --(1988)),--

Column 1, line 64, replace "Linn" with --(Linn--

Column 2, line 38, replace "mcrB" with --*mcrB*--

Column 2, line 39, replace "rglB" with --*rglB*--

Column 2, line 52, replace "mcrBC" with --*mcrBC*--

Column 3, line 8, replace "mcrB" with --*mcrB*--

Column 3, line 17, replace "mcrB" with --*mcrB*--

Column 3, line 18, replace "mcrB" with --*mcrB*--

Column 3, line 31, replace "E.coli" with --*E. coli*--

Column 3, line 59, replace "mcrB" with --*mcrB*--

Column 4, line 10, replace "rglB" with --*rglB*--

Column 4, line 25, replace "Ehrlick" with --Ehrlich--

Column 4, line 34, replace "Capowski" with --(Capowski--

UNITED STATES PATENT AND TRADEMARK OFFICE

CERTIFICATE OF CORRECTION

PATENT NO.: 5,405,760

DATED: April 11, 1995

INVENTOR(S): Raleigh, et al.

It is certified that errors appear in the above-identified patent and that said Letters Patent is hereby corrected as shown below:

Column 4, line 36, replace "Chandler" with --(Chandler--

Column 4, line 38, replace "animals Bestor" with --animals (Bestor--

Column 4, line 50, replace "Raleigh, et al., Raleigh, et al., with --Raleigh, et al.--

Column 5, line 46, replace "MspI" with --*MspI*--

Column 5, line 47, replace "HpaII" with --*HpaII*--

Column 5, line 50, replace "MspI" with --*MspI*--

Column 5, line 51, replace "HpaII" with *HpaII*--

Column 5, line 52, replace "GG" with --CG--

Column 5, line 61, replace "MspI/HpaII" with --*MspI*/*HpaII*--

Column 5, line 64, replace "XmaI/SmaI" with --*XmaI*/*SmaI*--

Column 5, line 65, replace "AccII/BspMII" with --*AccII*/*Bsp*MII--

Column 5, line 66, replace "MspI/HpaII" with --*MspI*/*HpaII*--

Column 5, line 67, replace "AsuII/Csp45I" with --*AsuII*/*Csp*45I--

Column 6, line 18, replace "PGR" with --PCR--

Column 6, lines 33-34, replace "Escherichia coli" with --*Escherichia coli*--

Column 6, lines 41-42, replace "desirables" with --desirable--

UNITED STATES PATENT AND TRADEMARK OFFICE

CERTIFICATE OF CORRECTION

PATENT NO.: 5,405,760

DATED: April 11, 1995

INVENTOR(S): Raleigh, et al.

It is certified that errors appear in the above-identified patent and that said Letters Patent is hereby corrected as shown below:

Column 7, line 18, replace "mcrBC" with --*mcrBC*--

Column 7, line 19, replace "E.coli" with --*E. coli*--

Column 7, line 23, replace "mcrBC" with --*mcrBC*--

Column 8, line 23, replace "Escherichia coli" with --*Escherichia coli*--

Column 8, line 32, replace "E.coli" with --*E. coli*--

Column 8, line 33-34, replace "E.coli" with --*E. coli*--

Column 8, line 35, replace "NAC1" with --NaCl--

Column 8, line 58, replace "SphI" with --*Sph*I--

Column 8, line 58, replace "Aat1I" with --*Aat*II--

Column 8, line 60, replace "AatII" with --*Aat*II--

Column 8, line 62, replace "mcrB" with --*mcrB*--

Column 8, line 63, replace "mcrC" with --*mcrC*--

Column 8, line 67, repalce "(recA::Cam)" with --(*recA*::Cam)--

Column 9, line 7, replace "mcrB" with --*mcrB*--

Column 9, line 7, replace "mcrC" with --*mcrC*--

UNITED STATES PATENT AND TRADEMARK OFFICE
CERTIFICATE OF CORRECTION

PATENT NO.:     5,405,760                    Page 4 of 15

DATED:          April 11, 1995

INVENTOR(S):    Raleigh, et al.

It is certified that errors appear in the above-identified patent and that said Letters Patent is hereby corrected as shown below:

Column 9, line 7, replace "EcoRI" with --*Eco*RI--

Column 9, line 20, replace "ClaI" with --*Cla*I--

Column 9, line 20, replace "AluI" with --*Alu*I--

Column 9, line 21, replace "AluI" with --*Alu*I--

Column 9, line 27, replace "and0.6" with --and 0.6--

Column 9, line 29, replace "the2.3" with --the 2.3--

Column 9, line 52, replace "mcrB" with --*mcr*B--

Column 10, line 55, replace "mcrB" with --*mcr*B--

Column 10, line 58, replace "mcrB" with --*mcr*B--

Column 10, line 65, replace "mcrB" with --*mcr*B--

Column 11, line 8, replace "in vivo" with --*in vivo*--

Column 11, line 16, replace "M.AluI" with --M.*Alu*I--

Column 11, line 18, replace "M.AluI" with --M.*Alu*I--

UNITED STATES PATENT AND TRADEMARK OFFICE
CERTIFICATE OF CORRECTION

PATENT NO. : 5,405,760

DATED : April 11, 1995

INVENTOR(S) : Raleigh, et al.

It is certified that error appears in the above-indentified patent and that said Letters Patent is hereby corrected as shown below:

Column 11, line 18, replace "AluI" with --*Alu*I--

Column 11, line 19, replace "AflIII" with --*Afl*III--

Column 11, line 23, replace "M.HaeIII" with --M.*Hae*III--

Column 11, line 24, replace "AflIII" with --*Afl*III--

Column 11, line 28, replace "M.HhaI" with --M.*Hha*I--

Column 11, line 29, replace "M.HhaI" with --M.*Hha*I--

Column 11, line 30, replace "AflIII" with --*Afl*III--

Column 11, line 33, replace "M.MspI" with --M.*Msp*I--

Column 11, line 34, replace "AflIII" with --*Afl*III--

Column 11, line 37, replace "M.SssI" with --M.*Sss*I--

Column 11, line 37 replace "M.SssI" with --M.*Sss*I--

Column 11, line 39, replace "Escherichia coli" with --*Escherichia coli*--

Column 11, line 40, replace "M.PvuII" with --M.*Pvi*II--

Column 11, line 43, replace "M.HpaI" with --M.*Hpa*I--

Column 11, ine 46, replace "M.HpaI" with --M.*Hpa*I--

UNITED STATES PATENT AND TRADEMARK OFFICE
CERTIFICATE OF CORRECTION

PATENT NO. : 5,405,760

DATED : April 11, 1995

INVENTOR(S) : Raleigh, et al.

It is certified that error appears in the above-indentified patent and that said Letters Patent is hereby corrected as shown below:

Column 11, lines 52-53, replace "doubles-tranded" with --double-stranded--

Column 12, line 21 replace "with." with --with--

Column 12, line 23, replace "in situ" with --*in situ*--

Column 12, line 24, replace "in situ" with --*in situ*--

Column 13, line 57, replace "stimulators factor" with --stimulatory factors--

Column 13, lines 66-67, replace "Escherichia coli" with --*Escherichia coli*--

Column 13, last line, replace "McrBG" with --McrBC--

Column 14, line 10, replace "Escherichia coli" with --*Escherichia coli*--

UNITED STATES PATENT AND TRADEMARK OFFICE

CERTIFICATE OF CORRECTION

PATENT NO.:     5,405,760

DATED:          April 11, 1995

INVENTOR(S):    Raleigh, et al.

It is certified that errors appear in the above-identified patent and that said Letters Patent is hereby corrected as shown below:

Column 14, line 37, replace "stimulators" with --stimulatory--

Column 14, line 45, replace "stimulators" with --stimulatory--

Column 15, line 4, replace "mcrBC$_{K12}$" with --*mcrBC*$_{K12}$--

Column 15, lines 9-10, replace "Proteus vulgaris" with --*Proteus vulgaris*--

Column 15, line 11, replace "E. coli" with --*E. coli*--

Column 15, line 17, replace "intergenie" with --intergenic--

Column 15, line 20, replace "E. coli" with --*E. coli*--

Column 15, line 21, replace "EcoK" with -- *EcoB*--

Column 15, line 21, replace "EcoA" with --*EcoA*--

Column 15, line 22, replace "mcrBC" with --*mcrBC*--

Column 15, line 23, replace "hsd" with --*hsd*--

Column 15, line 24, replace "mcrBC" with --*mcrBC*--

Column 15, line 26, replace "hsds" and "mcrB" with
    --*hsdS*-- and *mcrB*--

Column 15, line 29, replace "mcrBC" with --*mcrBC*--

Column 15, line 54, replace "mcrBC" with --*mcrBC*--

Column 15, line 57, replace "mcrBC" with --*mcrBC*--

Page 7 of 15

UNITED STATES PATENT AND TRADEMARK OFFICE
CERTIFICATE OF CORRECTION

PATENT NO.: 5,405,760

DATED: April 11, 1995

INVENTOR(S): Raleigh, et al.

It is certified that errors appear in the above-identified patent and that said Letters Patent is hereby corrected as shown below:

Column 15, line 58, replace "McrBC" with --*McrBC*--

Column 16, line 9, replace "McrBK12" with --*McrBC*$_{K12}$--

Column 16, line 58, replace "Escherichia coli" with --*Escherichia coli*--

Column 16, line 60, replace "NACl" with --NaCl--

Column 17, line 15, replace "35 X g" with 35 X *g*--

Column 17, line 39, replace "NACl" with --NaCl--

Column 17, line 57, replace "Ilia." with --IIIa--

Column 18, line 2, replace "DNAX" with --DNA--

Column 18, line 64, replace "0..5" with --0.5--

Column 19, line 38, replace "NACl" with --NaCl--

Column 19, line 63, replace "AluI" with --*Alu*I--

Column 19, line 63, replace "ClaI" with --*Cla*I--

Column 20, line 26, replace "tile" with --the--

Column 20, line 39, replace "AluI" with --*Alu*I--

Column 20, line 41, replace "AluI" with --*Alu*I--

Column 20, line 42, replace "ClaI" with --*Cla*I--

Column 20, line 44, replace "AflIII" with --*Afl*III--

UNITED STATES PATENT AND TRADEMARK OFFICE

CERTIFICATE OF CORRECTION

PATENT NO.:   5,405,760

DATED:        April 11, 1995

INVENTOR(S):  Raleigh, et al.

It is certified that errors appear in the above-identified patent and that said Letters Patent is hereby corrected as shown below:

Column 20, line 45, replace "NdeI" with --*NdeI*--

Column 20, line 45, replace "SspI" with --*SspI*--

Column 21, line 10, replace "M.AluI", "M.HaeI", "M.HhaI" and "M.MspI" with --M.*AluI*--, --M.*HaeI*--, --M.*HhaI*-- and --M.*MspI*--

Column 21, line 11, replace "M.HpaI" with --M.*HpaI*--

Column 21, line 49, replace "pUG19" with --pUC19--

Column 21, line 55, replace "M.HaeIII" with --M.*HaeIII*--

Column 22, line 24, replace "not;" with --not--

Column 22, line 42, replace "Judged" with --judged--

Column 24, line 46, replace "M.AluI" with --M.*AluI*--

Column 25, line 20, replace "mcrBG" with --*mcrBC*--

Column 25, line 25, replace "M.AluI" with --M.*AluI*--

Column 27-28, In Table III, SubNo. 1, replace "+ +" with -- * *--

Column 30, line 43, relace "HinDPI" with --*HindPI*--

Column 30, line 55, replace "I11" with --III--

Column 30, line 59, replace "at" with --as--

Column 31, line 50, replace "δ" with -- γ --

UNITED STATES PATENT AND TRADEMARK OFFICE

CERTIFICATE OF CORRECTION

PATENT NO.:     5,405,760

DATED:          April 11, 1995

INVENTOR(S):    Raleigh, et al.

It is certified that errors appear in the above-identified patent and that said Letters Patent is hereby corrected as shown below:

Column 32, line 19, replace "mcrB" with --*mcr*B--

Column 32, line 20, replace "mcrC" with --*mcr*C--

Column 33, line 1, replace "MaNail" with --MacNeil--

Column 33, line 4, replace "mcrB" with --*mcr*B--

Column 33, line 18, replace "E. coli" with --*E. coli*--

Column 36, line 15, replace "NAC1" with --NaCl--

Column 36, line 24, replace "0.2-1M" with --0.2-1 M--

Col. 36, line 31, replace "0.7M" with --0.7 M--

Column 36, line 56, replace "McrG" with --McrC--

Column 37, line 27, replace "gone(s)" with --gene(s)--

Column 37, line 28, replace "gone(s)" with --gene(s)--

Column 37, line 59, replace "RmC" with --R$^m$C--

Col. 39, line 62, replace "mcrB" with --*mcr*B--

Column 39, line 63, replace "mcrC" with --*mcr*C--

Column 39, line 64, replace "mcrB" with --*mcr*B--

Column 40, line 3, replace "mcrB" with --*mcr*B--

Column 40, line 5, replace "mcrC" with --*mcr*C--

UNITED STATES PATENT AND TRADEMARK OFFICE

CERTIFICATE OF CORRECTION

PATENT NO.:    5,405,760

DATED:         April 11, 1995

INVENTOR(S):   Raleigh, et al.

It is certified that errors appear in the above-identified patent and that said Letters Patent is hereby corrected as shown below:

Column 40, line 8, replace "Prime" with --Primer--

Column 40, line 9, replace "#3'" with --#3--

Column 40, line 47, replace "mcrB" and "mcrC" with --*mcr*B-- and --*mcr*C--

Column 40, line 58, replace "mcrB" with --*mcr*B--

Column 40, line 64, replace "mcrC" with --*mcr*C--

Column 41, line 14, replace "mcrBC" with --*mcr*BC--

Column 41, line 16, replace "mcrBC" with --*mcr*BC--

Column 41, line 21, replace "mcrBC" with --*mcr*BC--

Column 42, line 9, replace "NSiI" with --*Nsi*I--

Column 42, line 19, replace "methtonine" with --methionine--

Column 50, line 24, replace "(N40-100)5m5c" with --(N40-100)Rm5C--

UNITED STATES PATENT AND TRADEMARK OFFICE
CERTIFICATE OF CORRECTION

PATENT NO. : 5,405,760  
DATED : April 11, 1995  
INVENTOR(S) : Raleigh, et al.

Page 12 of 15

It is certified that error appears in the above-indentified patent and that said Letters Patent is hereby corrected as shown below:

Column 11, line 49, after "favorably" insert
--TABLE I

| Substrate | Position of McrBC site relative to end of linears | | Position relative to GenBank original | Position relative to linear end of mC(1) | Position relative to linear end of mC(2) | Sequence surrounding modified sites ($*C=m^5C$) | $N(\gamma)$ † |
|---|---|---|---|---|---|---|---|
| pBR.AluI-Cla | 2068 |   | 2092 | 2043 | 2092 | aG*Ct ($N_x$) aG*Ct | 48 |
|   | 2062 | (A) | 2086 | 2032 | 2092 | tC*Ga ($N_x$) tC*Ga | 59 |
|   | 2731 | (B) | 2755 | 2708 | 2754 | " " | 45 |
|   | 3664 | (C) | 3688 | 3632 | 3695 | " " | 62 |
|   | 2004 | (D) | 2028 | 1975 | 2032 | " " | 56 |
| pUC.AluI-Afl |   | 384 | 258 | 362 | 407 | " " | 44 |
|   |   | 374 | 248 | 340 | 407 | " " | 66 |
|   |   | 2410 | 2284 | 2387 | 2433 | " " | 45 |
|   |   | 213 | 87 | 181 | 245 | " " | 63 |
|   |   | 1478 | 1352 | 1446 | 1509 | " " | 61 |
| pUC.HaeIII-Afl |   | 1721 | 1595 | 1675 | 1765 | gG*Cc ($N_x$) gG*CC cC*Gg ($N_x$) cC*Gg | 79 |
| pUC.HhaI-Afl |   | 189 | 63 | 156 | 221 | G*Cg c ($N_x$) G*Cg c c gC*G ($N_x$) g cC*G | 64 |
|   |   | 2478 | 2352 | 2444 | 2511 | " " | 66 |
|   |   | 126 | 0 | 95 | 156 | " " | 60 |
| pUC.MspI-Afl |   | 1650 | 1524 | 1616 | 1683 | c*ccgg c ($N_x$) t*ccgg c g ggcC*G ($N_x$) a ggcC*G | 66 |

UNITED STATES PATENT AND TRADEMARK OFFICE
CERTIFICATE OF CORRECTION

PATENT NO. : 5,405,760

DATED : April 11, 1995

INVENTOR(S) : Raleigh, et al.

It is certified that error appears in the above-indentified patent and that said Letters Patent is hereby corrected as shown below:

Weak sites

| | | | | | | | |
|---|---|---|---|---|---|---|---|
| pBR.AluI-Cla | 2663 | (e) | 2687 | 2618 | 2708 | aG*Ct ($N_x$) aG*Ct<br>tC*Ga ($N_x$) tC*Ga | 89 |
| | 3582 | (f) | 3606 | 3532 | 3632 | "  " | 99 |
| pUC.AluI-Afl | | 454 | 324 | 407 | 502 | "  " | 95 |
| pUC.HaeIII-Afl | | 472 | 346 | 421 | 523 | gG*Cc ($N_x$) gG*CC<br>cC*Gg ($N_x$) cC*Gg | 101 |
| | | 672 | 546 | 523 | 821 | " | 297 |
| pUC.HhaI-Afl | | 1622 | 1496 | 1575 | 1668 | G*Cg c ($N_x$) G*Cg c<br>c gC*G ($N_x$) g cC*G | 92 |
| | | 754 | 628 | 703 | 804 | "  " | 100 |
| pUCMspI-Afl | | 1666 | 1540 | 1616 | 1717 | c*ccgg c ($N_x$) G*Ccgg t<br>g ggcC*G ($N_x$) c ggcC*A | 100 |
| | | 1560 | 1434 | 1503 | 1616 | A*Ccgg a ($N_x$) c*ccgg c<br>t ggcc*t ($N_x$) g ggcC*G | 112 |

UNITED STATES PATENT AND TRADEMARK OFFICE

CERTIFICATE OF CORRECTION

PATENT NO.: 5,405,760

DATED: April 11, 1995

INVENTOR(S): Raleigh, et al.

It is certified that errors appear in the above-identified patent and that said Letters Patent is hereby corrected as shown below:

Column 11, line 49, after Table I, insert

--§ Cleavage position was roughly mapped by double digestion (for pBR322.AluI) or by considering partial digest product sizes in conjuction with positions of modification. The number given is the average of mC(1) and mC(2) from columns 4 and 5, using those modified positions closest to the mapped cleavage position. The numbers are relative to the end of the linearized plasmid.

¶ Cleavage position adjusted to reflect the sequences presented in Genbank with correction by Watson (Gene 70:399 1988).

• position of modification in the sequence was obtained as follows: the UWGCG FIND program was used to find the restriction enzyme recognition site (the number of the 5' base of the sequence is given by this) and surrounding sequence; the number of bases between the modified base and the 5' end of the recognition site was added to this. For M.AluI and M. HaeIII, this number was 2; for M.HhaI, it was 1. For M.MspI, the numbers were counted by hand because only the modified C with a purine to the 5' site was considered, and these were sometimes on the strand opposite to that for which numbering was obtained.

UNITED STATES PATENT AND TRADEMARK OFFICE
CERTIFICATE OF CORRECTION

PATENT NO. : 5,405,760
DATED : April 11, 1995
INVENTOR(S) : Raleigh, et al.

It is certified that error appears in the above-indentified patent and that said Letters Patent is hereby corrected as shown below:

† $N_{(Y)} - mC(2) - mC(1) - 1$: this is the number in the scheme $R^{m}C(N_y)R^{m}C$. It is one less than the spacing number in FIGs. 7A and B, which is $mC(2) - mC(1)$.--

Signed and Sealed this

Third Day of December, 1996

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 42 base pairs
( B ) TYPE: nucleic acid
( C ) STRANDEDNESS: unknown
( D ) TOPOLOGY: unknown ( i x ) FEATURE:
( A ) NAME/KEY: CDS
( B ) LOCATION: 16..42

( x i ) SEQUENCE DESCRIPTION: SEQ ID NO:1:

AATAGAGGCT TAGCA ATG AGG AAG GCA TAT CTT ATG GAA TCT    42

```
              Met Arg Lys Ala Tyr Leu Met Glu Ser
                1               5
```

( 2 ) INFORMATION FOR SEQ ID NO:2:

( i ) SEQUENCE CHARACTERISTICS:
        ( A ) LENGTH: 60 base pairs
        ( B ) TYPE: nucleic acid
        ( C ) STRANDEDNESS: unknown
        ( D ) TOPOLOGY: unknown ( i x ) FEATURE:
        ( A ) NAME/KEY: CDS
        ( B ) LOCATION: 13..60

( x i ) SEQUENCE DESCRIPTION: SEQ ID NO:2:

```
TAAACAACAG AA ATG GAC CAA CAA ATT ATT AGG GGA CTC ATA GTG GAA      48
              Met Asp Gln Gln Ile Ile Arg Gly Leu Ile Val Glu
                1               5                  10
CAG CCC GTG ATA                                                   60
Gln Pro Val Ile
            15
```

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:3:

```
CCCGGATTAC AGCCGTATTC CCG                                         23
```

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:4:

```
GCGCCGGTTT TGCCACTGGC ACGGCGG                                     27
```

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:5:

```
GGTGCAGGCG TTTATTGGAG TGATTGCCGG                                  30
```

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:6:

```
GGSCCSGGSG TSGGSAARAC S                                           21
```

( 2 ) INFORMATION FOR SEQ ID NO:7:

( i ) SEQUENCE CHARACTERISTICS:
  ( A ) LENGTH: 21 base pairs
  ( B ) TYPE: nucleic acid
  ( C ) STRANDEDNESS: unknown
  ( D ) TOPOLOGY: unknown ( x i ) SEQUENCE DESCRIPTION: SEQ ID NO:7:

GG W CC W GG W G T W GG W AARAC W- 21

( 2 ) INFORMATION FOR SEQ ID NO:8:

( i ) SEQUENCE CHARACTERISTICS:
    ( A ) LENGTH: 82 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:8:

AGGTTTACCG CAGCTGCCTC GCGCGTTTCG GTGATGACGG TGAAAACCTC TGACACATGC     60

AGCTCCCGGA GACGGTCACA GC     82

( 2 ) INFORMATION FOR SEQ ID NO:9:

( i ) SEQUENCE CHARACTERISTICS:
    ( A ) LENGTH: 24 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:9:

GAGGAAGGCA TATCATATGG AATC     24

( 2 ) INFORMATION FOR SEQ ID NO:10:

( i ) SEQUENCE CHARACTERISTICS:
    ( A ) LENGTH: 24 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:10:

CGGGATCCGA CAGGTATCAC GGGC     24

( 2 ) INFORMATION FOR SEQ ID NO:11:

( i ) SEQUENCE CHARACTERISTICS:
    ( A ) LENGTH: 28 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:11:

CCCCTATAAA CAACACATAT GGACCAAC     28

( 2 ) INFORMATION FOR SEQ ID NO:12:

( i ) SEQUENCE CHARACTERISTICS:
    ( A ) LENGTH: 24 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:12:

CGGGATCCCT ATAAAACTTA CCGC     24